(12) United States Patent
Jafarishad et al.

(10) Patent No.: US 10,792,037 B2
(45) Date of Patent: Oct. 6, 2020

(54) SUTURE PACKAGE

(71) Applicants: Hamed Jafarishad, Tehran (IR);
Masoud Rezaei Rejani, Tehran (IR);
Seyed Hassan Atyabi, Tehran (IR)

(72) Inventors: Hamed Jafarishad, Tehran (IR);
Masoud Rezaei Rejani, Tehran (IR);
Seyed Hassan Atyabi, Tehran (IR)

( * ) Notice: Subject to any disclaimer, the term of this patent is extended or adjusted under 35 U.S.C. 154(b) by 0 days.

(21) Appl. No.: 16/817,632

(22) Filed: Mar. 13, 2020

(65) Prior Publication Data
US 2020/0205809 A1 Jul. 2, 2020

Related U.S. Application Data

(60) Provisional application No. 62/817,589, filed on Mar. 13, 2019.

(51) Int. Cl.
*A61B 17/06* (2006.01)

(52) U.S. Cl.
CPC .............. *A61B 17/06133* (2013.01); *A61B 2017/06142* (2013.01)

(58) Field of Classification Search
CPC .... A61B 17/06133; A61B 2017/06142; A61B 17/04
USPC .............. 206/572, 63.3, 380, 225, 339
See application file for complete search history.

(56) References Cited

U.S. PATENT DOCUMENTS

| | | | | |
|---|---|---|---|---|
| 4,961,498 A | * | 10/1990 | Kalinski | A61B 17/06133 206/339 |
| 5,099,994 A | * | 3/1992 | Kalinski | A61B 17/06133 206/409 |
| 5,628,395 A | * | 5/1997 | Daniele | A61B 17/06133 206/227 |
| 5,655,652 A | * | 8/1997 | Sobel | A61P 31/04 206/63.3 |
| 5,715,942 A | * | 2/1998 | Li | A61B 17/04 206/339 |
| 6,016,905 A | * | 1/2000 | Gemma | A61B 17/06133 206/380 |
| 6,047,815 A | * | 4/2000 | Cerwin | A61B 17/06133 206/225 |
| 6,135,272 A | * | 10/2000 | Sobel | A61B 17/06133 206/380 |
| 6,138,440 A | * | 10/2000 | Gemma | A61B 17/06133 206/63.3 |
| 6,644,469 B2 | * | 11/2003 | Alpern | A61B 17/06133 206/380 |

(Continued)

*Primary Examiner* — Chun Hoi Cheung
(74) *Attorney, Agent, or Firm* — Bajwa IP Law Firm; Haris Zaheer Bajwa

(57) ABSTRACT

A suture package for storing sutures armed with needles. The suture package includes a base member with a base outer periphery and a top member with a top outer periphery. The base member includes a base outer wall extending upwardly from a top side of the base member and along the base outer periphery. The base outer wall includes a plurality of base teeth and a plurality of base intercostal spaces arranged alternatively around the base outer periphery. The top member includes a top outer wall extending downwardly from a bottom side of the top member and along the top outer periphery. The top outer wall includes a plurality of top teeth and a plurality of top intercostal spaces arranged alternatively around the top outer periphery.

13 Claims, 23 Drawing Sheets

(56) References Cited

U.S. PATENT DOCUMENTS

| | | | | |
|---|---|---|---|---|
| 6,804,937 B2* | 10/2004 | Dey | ................ | A61B 17/06133 206/63.3 |
| 7,520,382 B2* | 4/2009 | Kennedy | .......... | A61B 17/06133 206/63.3 |
| 7,637,369 B2* | 12/2009 | Kennedy | .......... | A61B 17/06133 206/63.3 |
| 2007/0227914 A1* | 10/2007 | Cerwin | ............ | A61B 17/06133 206/63.3 |
| 2018/0161031 A1* | 6/2018 | Sonawane | ........ | A61B 17/06114 |

* cited by examiner

100

105

SUTURE PACKAGE

CROSS-REFERENCE TO RELATED APPLICATION

This application claims the benefit of priority from pending U.S. Provisional Patent Application Ser. No. 62/817,589, filed on Mar. 13, 2019, and entitled "SUTURE PACKAGE AND A WINDING METHOD THEREOF," which is incorporated herein by reference in its entirety.

TECHNICAL FIELD

The present disclosure generally relates to packaging, and particularly, relates to packages for surgical needles and sutures.

BACKGROUND

Packages for surgical needles and sutures are well known in the art. Suture packages may consist of a foldable cardboard for receiving a suture. Such suture packages may also have needle parks for mounting needles. Suture packages are, generally, designed to protect needles and sutures during sterilization, shipping, and handling. Suture packages may further be designed to provide ease of removal of needles and sutures. Conventional plastic suture packages may also be available for protecting surgical needles and sutures. Plastic suture packages may typically have an oval shape or a circular shape with a peripheral suture channel for containing one or more sutures. A needle park may also be positioned interior to the peripheral suture channel for mounting surgical needles.

Plastic suture packages are believed to have several advantages over paper packages. For example, they may be easy to load, may tend to maintain a suture in a controlled position within a peripheral suture channel, and may provide ease of dispensing. Although present suture packages are known to function appropriately in containing surgical sutures and needles, there is a constant need for improved suture packages having a suture channel which can be readily utilized in automated suture winding apparatuses and has the capability of reducing incidence of suture lock-up when a suture is withdrawn from a package.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary suture package for storing sutures armed with needles. An exemplary suture package may include a base member with a base outer periphery and a top member with a top outer periphery. In an exemplary embodiment, the base member may include a base outer wall extending upwardly from a top side of the base member and along the base outer periphery.

In an exemplary embodiment, the base outer wall may include a plurality of base teeth and a plurality of base intercostal spaces. In an exemplary embodiment, the plurality of base teeth and the plurality of base intercostal spaces may be arranged alternatively around the base outer periphery.

In an exemplary embodiment, the top member may include a top outer wall extending downwardly from a bottom side of the top member and along the top outer periphery. In an exemplary embodiment, the top outer wall may include a plurality of top teeth and a plurality of top intercostal spaces. In an exemplary embodiment, the plurality of top teeth and the plurality of top intercostal spaces may be arranged alternatively around the top outer periphery. In an exemplary embodiment, each respective top tooth from the plurality of top teeth may be associated with a respective base intercostal space from the plurality of base intercostal spaces.

In an exemplary embodiment, each respective top tooth from the plurality of top teeth may be configured to fill the respective base intercostal space from the plurality of base intercostal spaces. In an exemplary embodiment, each respective top intercostal space from the plurality of top intercostal spaces may be associated with a respective base tooth from the plurality of base teeth. In an exemplary embodiment, each respective base tooth from the plurality of base teeth may be configured to fill the respective top intercostal space from the plurality of top intercostal spaces.

In an exemplary embodiment, the base outer wall and the top outer wall may be configured to form an engaged outer wall responsive to one or more base teeth from the plurality of base teeth filling respective top intercostal spaces from the plurality of top intercostal spaces and one or more top teeth from the plurality of top teeth filling respective base intercostal spaces from the plurality of base intercostal spaces. In an exemplary embodiment, a peripheral winding channel may be formed between the top side of the base member, the bottom side of the top member, and an inner side of the engaged outer wall.

In an exemplary embodiment, the suture package may further include a zipper device. In an exemplary embodiment, the zipper device may include a top edge including a bottom curved surface, a bottom edge including a top curved surface, and an oval-shaped opener disposed between the top curved surface and the bottom curved surface. In an exemplary embodiment, the oval-shaped opener may include a top oval surface and a bottom oval surface.

In an exemplary embodiment, the top oval surface and the bottom curved surface may define a top curved path between the oval-shaped opener and the top edge. In an exemplary embodiment, the top curved path may be associated with the top outer wall. In an exemplary embodiment, the top oval surface and the bottom curved surface may be configured to guide a section of the top outer wall to move along the top curved path.

In an exemplary embodiment, the bottom oval surface and the top curved surface may define a bottom curved path between the oval-shaped opener and the bottom edge. In an exemplary embodiment, the bottom curved path may be associated with the base outer wall. In an exemplary embodiment, the bottom oval surface and the top curved surface may be configured to guide a section of the base outer wall to move along the bottom curved path.

In an exemplary embodiment, the zipper device may be configured to disengage and then reengage a section of the engaged outer wall responsive to the zipper device passing through a first closed path at the section of the engaged outer wall. In an exemplary embodiment, the first closed path may be associated with the engaged outer wall.

In an exemplary embodiment, the zipper device may include an opener head. In an exemplary embodiment, the opener head may be configured to disengage the section of the engaged outer wall through splitting the engaged outer wall responsive to the zipper device moving along the first closed path. In an exemplary embodiment, the opener head may further be configured to guide a first top tooth from the plurality of top teeth to enter the top curved path after splitting the engaged outer wall. In an exemplary embodiment, the first top tooth may be associated with the section of the engaged outer wall. In an exemplary embodiment, the opener head may further be configured to guide a first base tooth from the plurality of base teeth to enter the bottom curved path after splitting the engaged outer wall. In an exemplary embodiment, the first base tooth may be associated with the section of the engaged outer wall.

In an exemplary embodiment, a distal end of the top edge and a distal end of the bottom edge may be configured to reengage a section of the base outer wall exiting the bottom curved path with an associated section of the top outer wall exiting the top curved path through urging a second top tooth from the plurality of top teeth to fill a respective base intercostal space from the plurality of base intercostal spaces and urging a second base tooth from the plurality of base teeth to fill a respective top intercostal space from the plurality of top intercostal spaces.

In an exemplary embodiment, the engaged outer wall may include an entrance portion. In an exemplary embodiment, the zipper device may be configured to be placed in the first closed path responsive to the zipper device being inserted into the entrance portion. In an exemplary embodiment, the zipper device may further include a suture guide channel which may be configured to receive the suture, keep the suture in touch with an end of the suture guide channel during movement of the zipper device along the first closed path, and guide the suture to be placed inside the peripheral winding channel responsive to movement of the zipper device along the first closed path.

In an exemplary embodiment, the suture package may further include a needle park configured to receive and hold a needle. In an exemplary embodiment, the needle park may include a base element and a flexible arm. In an exemplary embodiment, the base element may include a protruded edge and a slot present immediately next to the protruded edge.

In an exemplary embodiment, a proximal end of the flexible arm may be attached to a torsional spring. In an exemplary embodiment, a distal end of the flexible arm may be disposed inside the slot. In an exemplary embodiment, the flexible arm may be configured to deflect downwardly inside the slot responsive to the distal end of the flexible arm being pushed downward, guide the needle to be placed at a bottom side of the protruded edge, and secure the needle between the distal end of the flexible arm and a bottom surface of the protruded edge through applying an upward force to the needle. In an exemplary embodiment, the upward force may be associated with the torsional spring.

In an exemplary embodiment, the suture package my further include a first guide rod receiving hole. In an exemplary embodiment, the first guide rod receiving hole may be configured to receive a first guide rod. In an exemplary embodiment, the first guide rod may be configured to keep a section of the suture at a predetermined position during movement of the zipper device along the first closed path.

In an exemplary embodiment, the base member may further include a plurality of base flexible blades arranged around a base inner periphery of the base member. In an exemplary embodiment, each respective base flexible blade from the plurality of base flexible blades may be associated with a respective base tooth from the plurality of base teeth. In an exemplary embodiment, each respective base tooth may be attached to a distal end of the respective base flexible blade. In an exemplary embodiment, each respective base flexible blade may be configured to facilitate movement of the respective base tooth along the bottom curved path.

In an exemplary embodiment, the top member may further include a plurality of top flexible blades arranged around a top inner periphery of the top member. In an exemplary embodiment, each respective top flexible blade from the plurality of top flexible blades may be associated with a respective top tooth from the plurality of top teeth. In an exemplary embodiment, the respective top tooth may be attached to a distal end of the respective top flexible blade. In an exemplary embodiment, the respective top flexible blade may be configured to facilitate movement of the respective top tooth along the top curved surface.

In an exemplary embodiment, the suture package may further include a label attached to a top surface of the top member. In an exemplary embodiment, the label may include a label locker having a trapezoidal shape. In an exemplary embodiment, the label locker may be configured to rotate around a first axis. In an exemplary embodiment, the first axis may pass through a common edge of the label locker and the label.

In an exemplary embodiment, the top member may further include a trapping mechanism including a trapezoidal hole and a label gripper. In an exemplary embodiment, the trapezoidal hole may be associated with the label locker. In an exemplary embodiment, the label locker may be configured to rotate inside the trapezoidal hole. In an exemplary embodiment, the label gripper may be disposed at a bottom section of the trapezoidal hole. In an exemplary embodiment, the label gripper may be configured to bend downwardly responsive to the label locker pushing down the label gripper during rotation of the label gripper inside the trapezoidal hole and trap the label locker between the label gripper and an inner surface of the trapezoidal hole.

In an exemplary embodiment, the suture package may further include a lock mechanism. In an exemplary embodiment, the lock mechanism may include a wedge-shaped member attached to an inner surface of the base member and a lock hole provided at an inner surface of the top member. In an exemplary embodiment, the wedge-shaped member may include an inclined surface and a bottom surface. In an exemplary embodiment, the lock hole may be associated with the wedge-shaped member. In an exemplary embodiment, the lock hole may be configured to receive the wedge-shaped member. In an exemplary embodiment, the inclined surface may be configured to allow the wedge-shaped member to be inserted into the lock hole. In an exemplary embodiment, the bottom surface may be configured to prevent the wedge-shaped member to exit from the lock hole.

In an exemplary embodiment, the suture package may further include a second guide rod receiving hole. In an exemplary embodiment, the second guide rod receiving hole may be configured to receive a second guide rod. In an exemplary embodiment, the suture package may be configured to be positioned and fixed onto a base attached to the first guide rod and the second guide rod through inserting the first guide rod into the first guide rod receiving hole and inserting the second guide rod into the second guide rod receiving hole.

In an exemplary embodiment, the first guide rod receiving hole may have a circular shape. In an exemplary embodiment, the second guide rod receiving hole may have an elongated circular shape.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

Herein is disclosed an exemplary suture package for storing a suture armed with a needle. The exemplary suture package facilitates a winding process of a suture in a package. The exemplary suture package may also provide a facility for a physician to remove a suture from package easily by a low risk of suture lock-up.

Figure 1A:
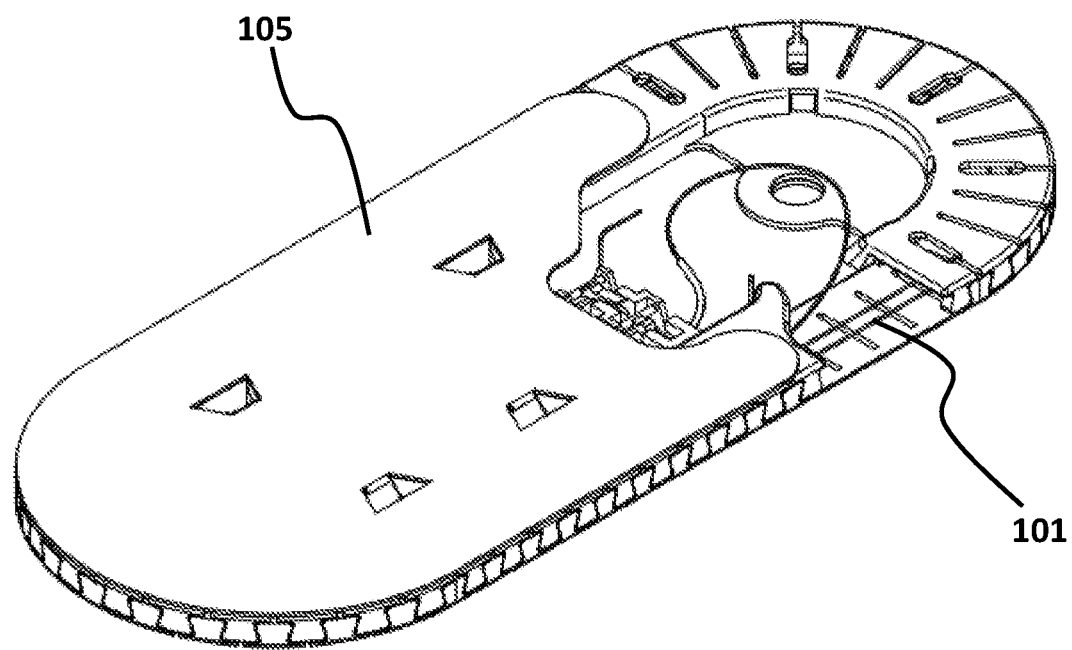
FIG. 1A illustrates an exemplary suture package, consistent with one or more exemplary embodiments of the present disclosure.
Figure 1B:
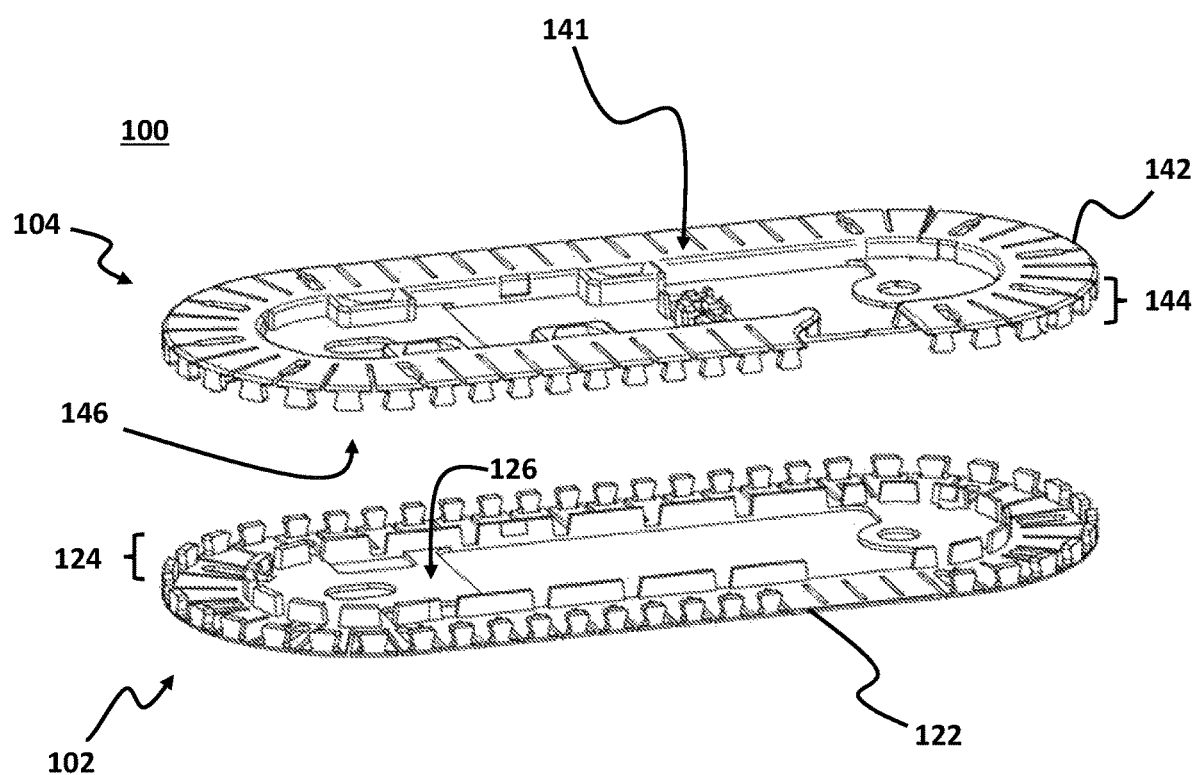
FIG. 1B illustrates an exploded view of an exemplary suture package, consistent with one or more exemplary embodiments of the present disclosure.

FIG. 1A shows an exemplary suture package 100, consistent with one or more exemplary embodiments of the present disclosure. As shown in FIG. 1A, in an exemplary embodiment, suture package 100 may be used to store a suture 101. FIG. 1B shows an exploded view of suture package 100, consistent with one or more exemplary embodiments of the present disclosure. As shown in FIG. 1B, in an exemplary embodiment, suture package 100 may include a base member 102 with a base outer periphery 122 and a top member 104 with a top outer periphery 142. In an exemplary embodiment, base member 102 may include a base outer wall 124 extending upwardly from a top side 126 of base member 102. In an exemplary embodiment, top side 126 of base member 102 may refer to a side of base member 102 which may face toward top member 104.

Figure 2:
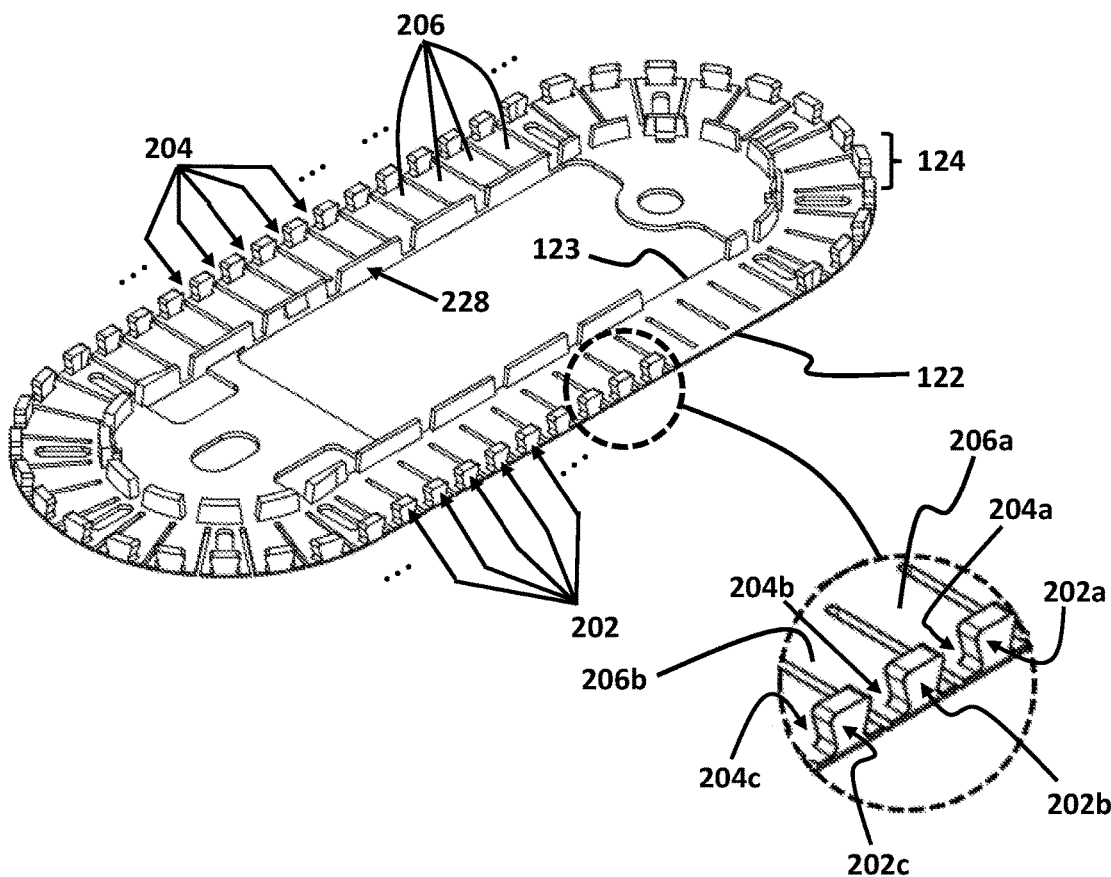
FIG. 2 illustrates a perspective view of a base member, consistent with one or more exemplary embodiments of the present disclosure.

FIG. 2 shows a perspective view of base member 102, consistent with one or more exemplary embodiments of the present disclosure. As shown in FIG. 2, in an exemplary embodiment, base outer wall 124 may include a plurality of base teeth 202 and a plurality of base intercostal spaces 204. In an exemplary embodiment, plurality of base teeth 202 and plurality of base intercostal spaces 204 may be arranged alternatively around base outer periphery 122.

For example, plurality of base teeth 202 may include a first base tooth 202a, a second base tooth 202b, and a third base tooth 202c. In an exemplary embodiment, plurality of base teeth 202 may include more base teeth in addition to first base tooth 202a, second base tooth 202b, and third base tooth 202c which are shown but not labeled in FIG. 2. In an exemplary embodiment, plurality of base intercostal spaces 204 may include a first base intercostal space 204a, a second base intercostal space 204b, and a third base intercostal space 204c. Furthermore, plurality of base intercostal spaces 204 may include more base intercostal spaces in addition to first base intercostal space 204a, second base intercostal space 204b, and third base intercostal space 204c. As further shown in FIG. 2, in an exemplary embodiment, first base intercostal space 204a may be present between first base tooth 202a and second base tooth 202b. Also, second base tooth 202b may be placed between first base intercostal space 204a and second base intercostal space 204b.

Referring back to FIG. 1B, in an exemplary embodiment, top member 104 may include a top outer wall 144 extending downwardly from a bottom side 146 of top member 104. In an exemplary embodiment, bottom side 146 of top member 104 may refer to a side of top member 104 which may face toward base member 102.

Figure 3:
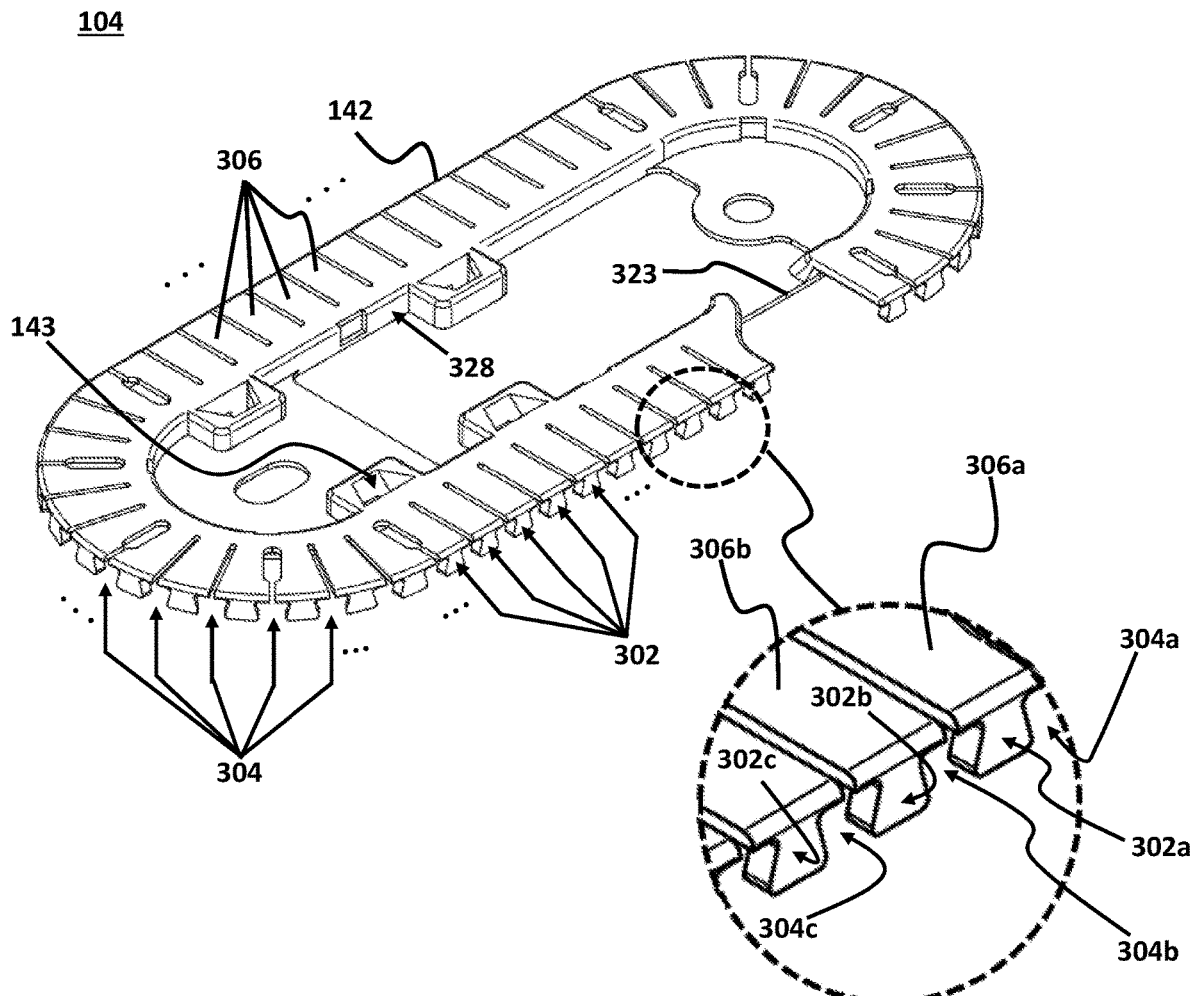
FIG. 3 illustrates a perspective view of a top member, consistent with one or more exemplary embodiments of the present disclosure.

FIG. 3 shows a perspective view of top member 104, consistent with one or more exemplary embodiments of the present disclosure. As shown in FIG. 3, in an exemplary embodiment, top outer wall 144 may include a plurality of top teeth 302 and a plurality of top intercostal spaces 304. In an exemplary embodiment, plurality of top teeth 302 and plurality of top intercostal spaces 304 may be arranged alternatively around top outer periphery 142.

For example, plurality of top teeth 302 may include a first top tooth 302a, a second top tooth 302b, and a third top tooth 302c. In an exemplary embodiment, plurality of top teeth 302 may include more top teeth in addition to first top tooth 302a, second top tooth 302b, and third top tooth 302c which are shown but not labeled in FIG. 3. In an exemplary embodiment, plurality of top intercostal spaces 304 may include a first top intercostal space 304a, a second top intercostal space 304b, and a third top intercostal space 304c. Furthermore, plurality of top intercostal spaces 304 may include more top intercostal spaces in addition to first top intercostal space 304a, second top intercostal space 304b, and third top intercostal space 304c. As further shown in FIG. 3, in an exemplary embodiment, second top intercostal space 304b may be placed between first top tooth 302a and second top tooth 302b. Also, second top tooth 302b may be present between second top intercostal space 304b and third top intercostal space 304c.

In an exemplary embodiment, each top tooth from may be associated with a respective base intercostal space from plurality of base intercostal spaces 204. In an exemplary embodiment, a size of each top tooth from plurality of top teeth 302 may coincide with or correspond to a size of the respective base intercostal space from plurality of base intercostal spaces 204 and also a shape of each top tooth from plurality of top teeth 302 may coincide with or correspond to a shape of the respective base intercostal space from plurality of base intercostal spaces 204. In an exemplary embodiment, each of plurality of top teeth 302 and each of plurality of base intercostal spaces 204 may have a trapezoidal shape. In an exemplary embodiment, trapezoidal shape of plurality of top teeth 302 and plurality of base intercostal spaces 204 may help base member 102 and top member 104 to be locked to each other when plurality of base intercostal spaces 204 are filled with plurality of top teeth 302. In an exemplary embodiment, each of plurality of top teeth 302 and each of plurality of base intercostal spaces 204 may have any other shapes. For example, first top tooth 302a may be associated with first base intercostal space 204a. In an exemplary embodiment, each top intercostal space from plurality of top intercostal spaces 304 may be associated with a respective base tooth from plurality of base teeth 202. For example, first top intercostal space 304a may be associated with first base tooth 202a. In an exemplary embodiment, association between each top tooth from plurality of top teeth 302 and a respective base intercostal space from plurality of base intercostal spaces 204 may refer to the fact that each top tooth from plurality of top teeth 302 may be present in front of a respective base intercostal space from plurality of base intercostal spaces 204.

In an exemplary embodiment, a size of each top intercostal space from plurality of top intercostal spaces 304 may coincide with or correspond to a size of the respective base tooth from plurality of base teeth 202 and also a shape of each top intercostal space from plurality of top intercostal spaces 304 may coincide with or correspond to a shape of the respective base tooth from plurality of base teeth 202. In an exemplary embodiment, each top intercostal space from plurality of top intercostal spaces 304 may be configured to be filled with the respective base tooth from plurality of base teeth 202. In an exemplary embodiment, each of plurality of top intercostal spaces 304 and each of plurality of base teeth 202 may have a trapezoidal shape. In an exemplary embodiment, trapezoidal shape of plurality of top intercostal spaces 304 and plurality of base teeth 202 may help base member 102 and top member 104 to be locked to each other when plurality of top intercostal spaces 304 are filled with plurality of base teeth 202. In an exemplary embodiment, each of plurality of top intercostal spaces 304 and each of plurality of base teeth 202 may have any other shapes.

As further shown in FIG. 2, in an exemplary embodiment, base member 102 may further include a plurality of base flexible blades 206 arranged around a base inner periphery 123. In an exemplary embodiment, a flexible blade may refer to a blade that may deflect under a relatively small force whereas a non-flexible blade may resist against deflection under relatively small forces. In an exemplary embodiment, it may be understood that a blade which have a relatively small thickness may function as a flexible blade. In an exemplary embodiment, plurality of base flexible blades 206 may include a first base flexible blade 206a and a second base flexible blade 206b. In an exemplary embodiment, each respective base flexible blade from plurality of base flexible blades 206 may be associated with a respective base tooth from plurality of base teeth 202. For example, first base flexible blade 206a may be associated with first base tooth 202a and second base flexible blade 206b may be associated with second base tooth 202b. In an exemplary embodiment, association between a respective base flexible blade from plurality of base flexible blades 206 and a respective base tooth from plurality of base teeth 202 may refer to attachment of the base flexible blade from plurality of base flexible blades 206 to the respective base tooth from plurality of base teeth 202. In an exemplary embodiment, each respective base tooth from plurality of base teeth 202 may be attached to a distal end of the respective base flexible blade from plurality of base flexible blades 206. For example, first base tooth 202a may be attached to a distal end of first base flexible blade 206a and second base tooth 202b may be attached to a distal end of second base flexible blade 206b. In an exemplary embodiment, each respective base flexible blade from plurality of base flexible blades 206 may be configured to facilitate movement of the respective base tooth along a curved path. For example, first base flexible blade 206a may facilitate movement of first base tooth 202a along bottom curved path 565. In an exemplary embodiment, it may be understood that flexibility feature of first base flexible blade 206a may allow first base flexible blade 206a to bend and/or deflect more easily and, to thereby, may allow first base tooth 202a to move more easily along a curved path. In an exemplary embodiment, plurality of base flexible blades 206 may be manufactured in such a way that create an integrated part.

As further shown in FIG. 3, in an exemplary embodiment, top member 104 may further include a plurality of top flexible blades 306 arranged around a top inner periphery 323. In an exemplary embodiment, plurality of top flexible blades 306 may include a first top flexible blade 306a and a second top flexible blade 306b. In an exemplary embodiment, each respective top flexible blade from plurality of top flexible blades 306 may be associated with a respective top tooth from plurality of top teeth 302. For example, first top flexible blade 306a may be associated with first top tooth 302a and second top flexible blade 306b may be associated with second top tooth 302b. In an exemplary embodiment, association between a respective top flexible blade from plurality of top flexible blades 306 and a respective top tooth from plurality of top teeth 302 may refer to attachment of respective top flexible blade from plurality of top flexible blades 306 to the respective top tooth from plurality of top teeth 302. In an exemplary embodiment, each respective top tooth from plurality of top teeth 302 may be attached to a distal end of the respective top flexible blade from plurality of top flexible blades 306. For example, first top tooth 302a may be attached to a distal end of first top flexible blade 306a and second top tooth 302b may be attached to a distal end of second top flexible blade 306b. In an exemplary embodiment, each respective top flexible blade from plurality of top flexible blades 306 may be configured to facilitate movement of the respective top tooth along top curved path 563. For example, first top flexible blade 306a may facilitate movement of first top tooth 302a along a curved path. In an exemplary embodiment, it may be understood that flexibility feature of first top flexible blade 306a may allow first top flexible blade 306a to bend and/or deflect more easily and, to thereby, may allow first top tooth 302a to move more easily along a curved path. In an exemplary embodiment, plurality of top flexible blades 306 may be manufactured in such a way that create an integrated part.

Figure 4:
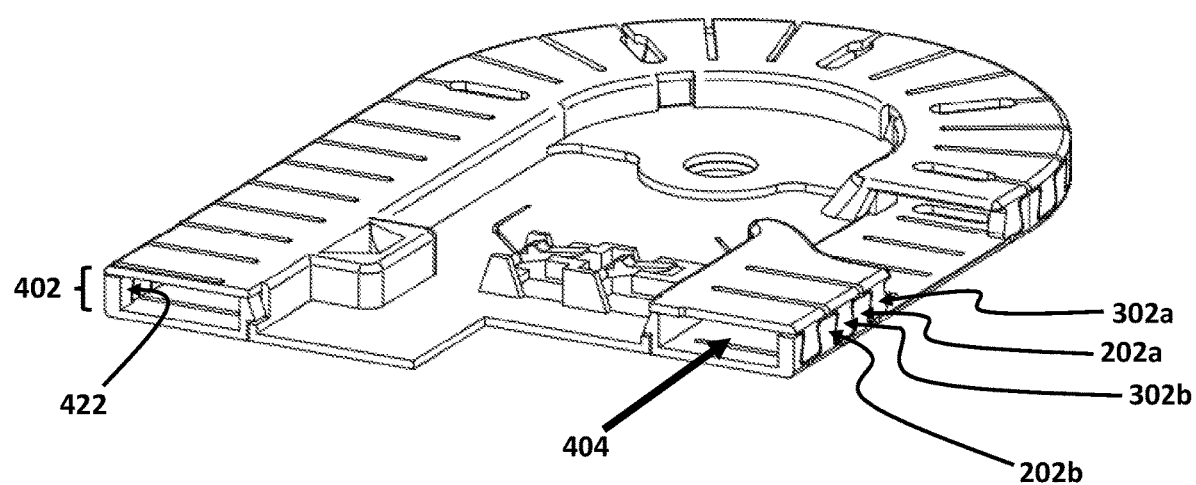
FIG. 4 illustrates a sectional view of a suture package, consistent with one or more exemplary embodiments of the present disclosure.

FIG. 4 shows a sectional view of suture package 100, consistent with one or more exemplary embodiments of the present disclosure. As shown in FIG. 4, an engaged outer wall 402 may be formed when base outer wall 124 is engaged with top outer wall 144. In an exemplary embodiment, base outer wall 124 may be engaged with top outer wall 144 when one or more base teeth from plurality of base teeth 202 fill respective top intercostal spaces from plurality of top intercostal spaces 304 and one or more top teeth from plurality of top teeth 302 fill respective base intercostal spaces from plurality of base intercostal spaces 204.

In an exemplary embodiment, as further shown in FIG. 4, a peripheral winding channel 404 may be formed between top side 126 of base member 102, bottom side 146 of top member 104, and an inner surface 422 of engaged outer wall 402. In an exemplary embodiment, peripheral winding channel 404 may be configured to receive and retain suture 101.

Figure 5A:
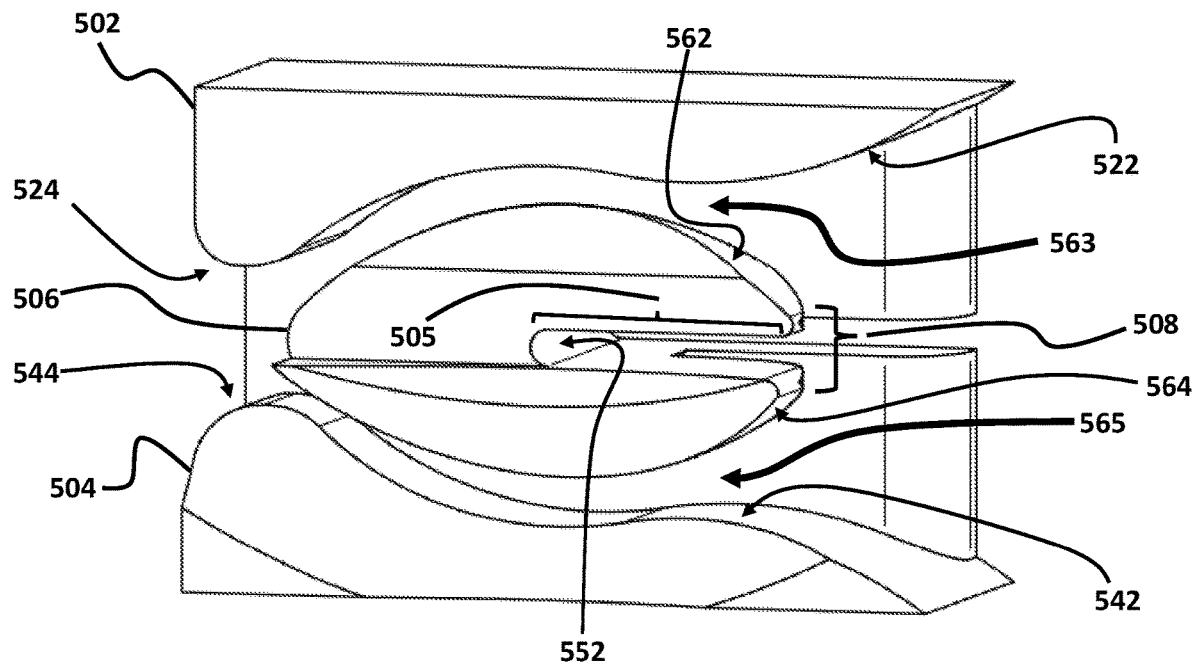
FIG. 5A illustrates a perspective view of a zipper device, consistent with one or more exemplary embodiments of the present disclosure.
Figure 5B:
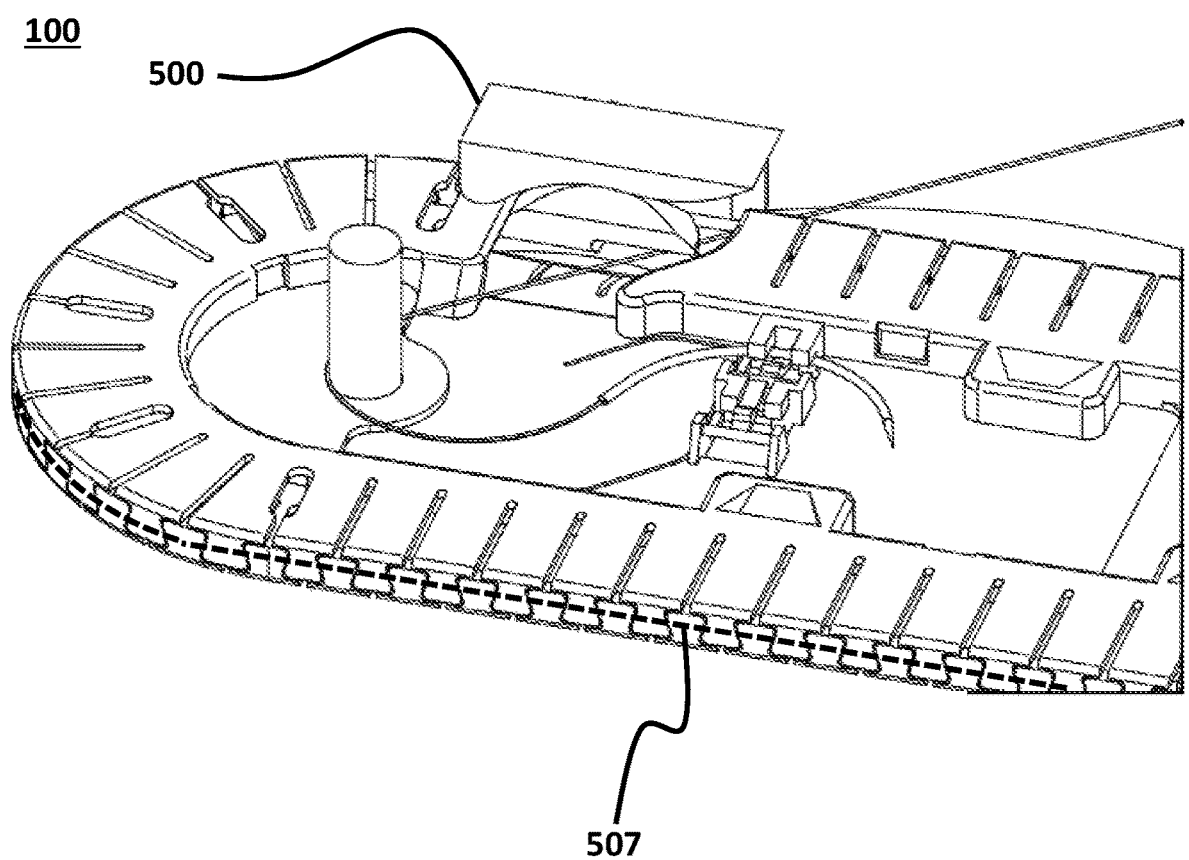
FIG. 5B illustrates a perspective view of a suture package with a zipper device, consistent with one or more exemplary embodiments of the present disclosure.

FIG. 5A shows a zipper device, consistent with one or more exemplary embodiments of the present disclosure. FIG. 5B shows a perspective view of suture package 100 with a zipper device, consistent with one or more exemplary embodiments of the present disclosure. As shown in FIG. 5A, in an exemplary embodiment, suture package 100 may further include a zipper device 500. In an exemplary embodiment, zipper device 500 may include a top edge 502 and a bottom edge 504. In an exemplary embodiment, top edge 502 may include a bottom curved surface 522. In an exemplary embodiment, bottom edge 504 may include a top curved surface 542. In an exemplary embodiment, zipper device 500 may further include an oval-shaped opener 506 disposed between top curved surface 542 and bottom curved surface 522.

In an exemplary embodiment, oval-shaped opener 506 may include a top oval surface 562 and a bottom oval surface 564. In an exemplary embodiment, top oval surface 562 and bottom curved surface 522 may define a top curved path 563 associated with top outer wall 144. In an exemplary embodiment, association between top curved path 563 and top outer wall 144 may refer to a configuration and a size of top curved path 563 which may allow top outer wall 144 to pass through top curved path 563. In an exemplary embodiment, top oval surface 562 and bottom curved surface 522 may be configured to guide a section of top outer wall 144 to move along top curved path 563.

In an exemplary embodiment, bottom oval surface 564 and top curved surface 542 may define a bottom curved path 565 associated with base outer wall 124. In an exemplary embodiment, association between bottom curved path 565 and base outer wall 124 may refer to a configuration and a size of bottom curved path 565 which may allow base outer wall 124 to pass through bottom curved path 565. In an exemplary embodiment, bottom oval surface 564 and top curved surface 542 may be configured to guide a section of base outer wall 124 to move along bottom curved path 565.

Figure 5C:
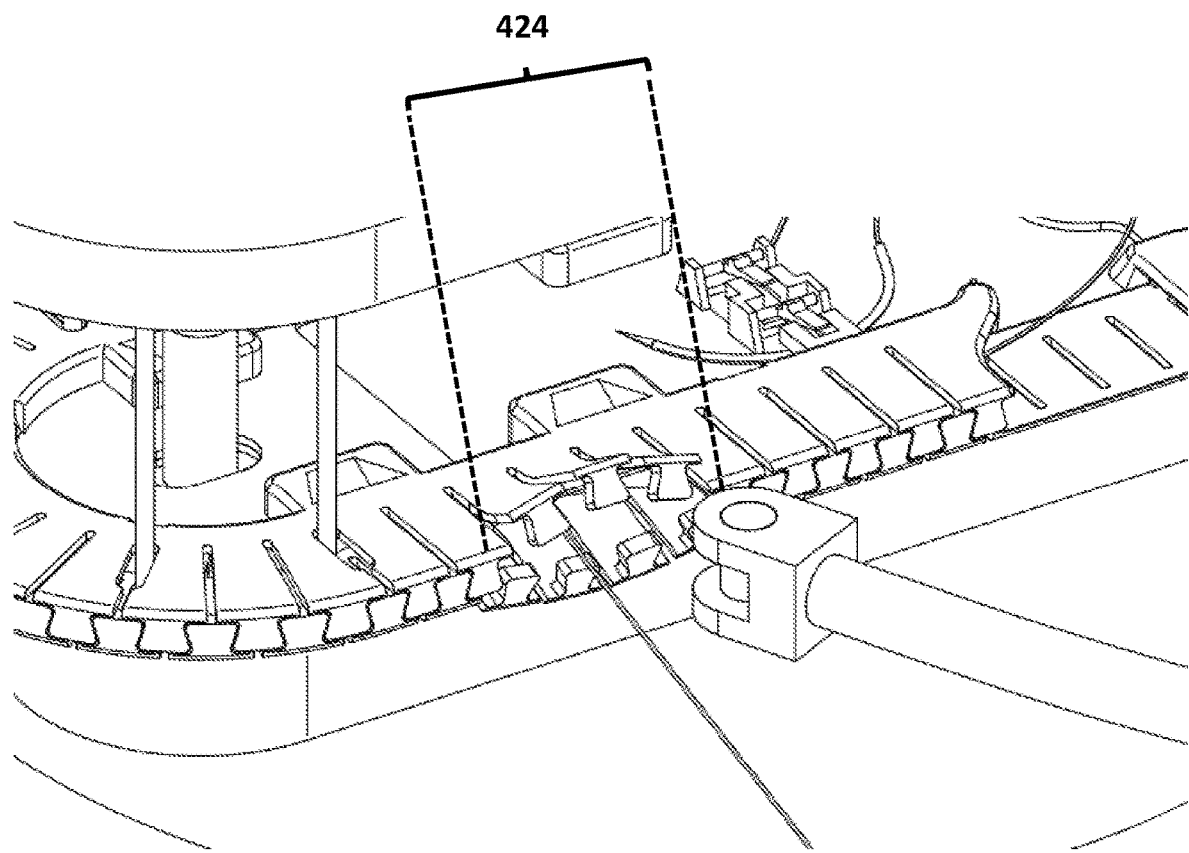
FIG. 5C illustrates a section of an engaged outer wall disengaged by a zipper device, consistent with one or more exemplary embodiments of the present disclosure.
Figure 5D:
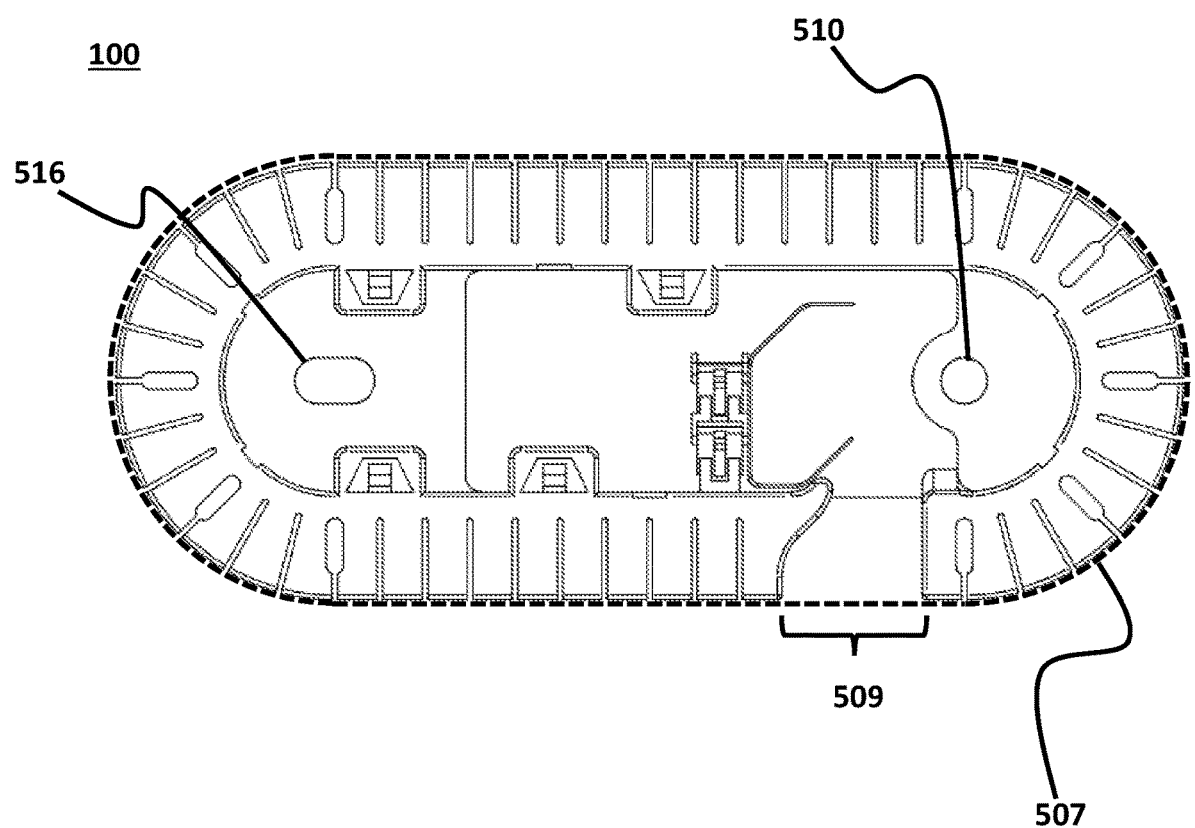
FIG. 5D illustrates a top view of a suture package, consistent with one or more exemplary embodiments of the present disclosure.

FIG. 5D shows a top view of suture package 100, consistent with one or more exemplary embodiments of the present disclosure. In an exemplary embodiment, zipper device 500 may be configured to disengage and then reengage a section of engaged outer wall 402 when zipper device 500 passes through a first closed path 507. In an exemplary embodiment, first closed path 507 may be associated with engaged outer wall 402.

As further shown in FIG. 5A, in an exemplary embodiment, zipper device 500 may further include an opener head 508. In an exemplary embodiment, opener head 508 may be configured to split and disengage a section of engaged outer wall 402 when zipper device 500 moves along first closed path 507. In an exemplary embodiment, opener head 508 may guide a top tooth from plurality of top teeth 302 to enter top curved path 563 and guide a base tooth from plurality of base teeth 202 to enter bottom curved path 565 after splitting and disengaging engaged outer wall 402. FIG. 5C shows a section 424 of engaged outer wall 402 disengaged by zipper device 500, consistent with one or more exemplary embodiments of the present disclosure.

In an exemplary embodiment, a distal end 524 of top edge 502 and a distal end 544 of bottom edge 504 may be configured to reengage a section of base outer wall 124 exiting bottom curved path 565 with an associated section of top outer wall 144 exiting top curved path 563 through urging a top tooth from plurality of top teeth 302 to fill an associated base intercostal space from plurality of base intercostal spaces 204 and urging a base tooth from plurality of base teeth 202 to fill an associated top intercostal space from plurality of top intercostal spaces 304. In an exemplary embodiment, reengaging a section of base outer wall 124 exiting bottom curved path 565 with an associated section of top outer wall 144 exiting top curved path 563 may refer to reengaging a section of base outer wall 124 exiting bottom curved path 565 with a section of top outer wall 144 that may be present in front of the section of base outer wall 124 exiting bottom curved path 565. In an exemplary embodiment, urging a top tooth from plurality of top teeth 302 to fill an associated base intercostal space from plurality of base intercostal spaces 204 may refer to urging a top tooth from plurality of top teeth 302 to fill a base intercostal space from plurality of base intercostal spaces 204 which may be present in front of the top tooth from plurality of top teeth 302. In an exemplary embodiment, urging a base tooth from plurality of base teeth 202 to fill an associated top intercostal space from plurality of top intercostal spaces 304 may refer to urging a base tooth from plurality of base teeth 202 to fill a top intercostal space from plurality of top intercostal spaces 304 which may be present in front of the base tooth from plurality of base teeth 202.

Figure 5E:
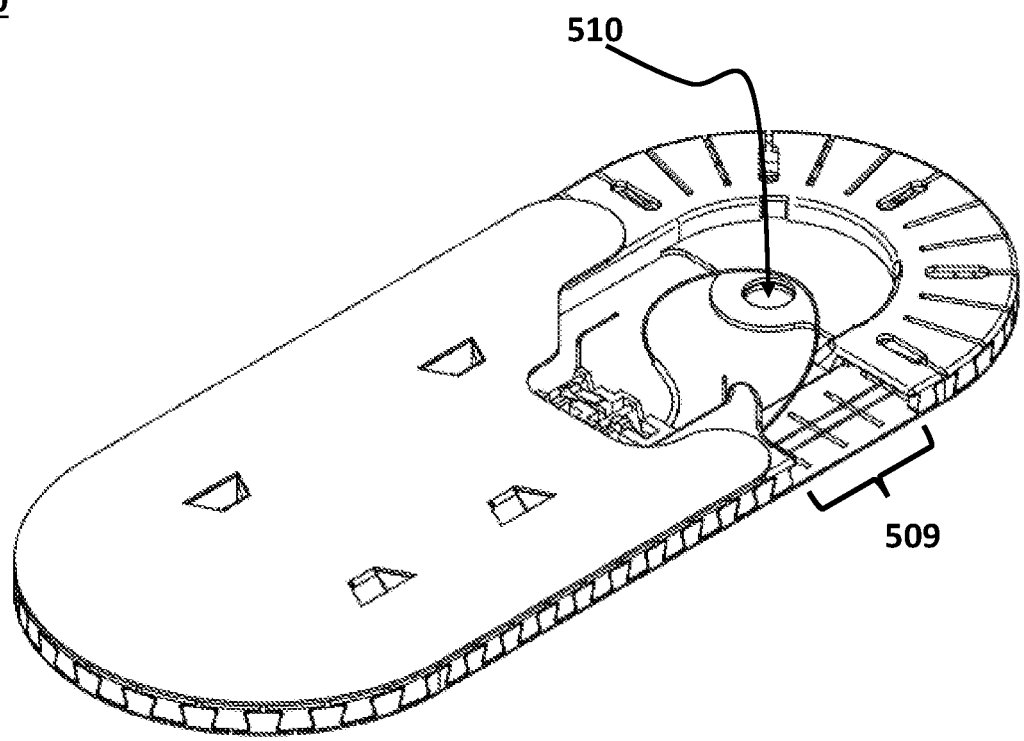
FIG. 5E illustrates a perspective view of a suture package, consistent with one or more exemplary embodiments of the present disclosure.

FIG. 5E shows a perspective view of suture package 100, consistent with one or more exemplary embodiments of the present disclosure. As shown in FIG. 5D, and FIG. 5E, in an exemplary embodiment, engaged outer wall 402 may include an entrance portion 509. In an exemplary embodiment, zipper device 500 may be placed in first closed path 507 when zipper device 500 is inserted into entrance portion 509.

Figure 5F:
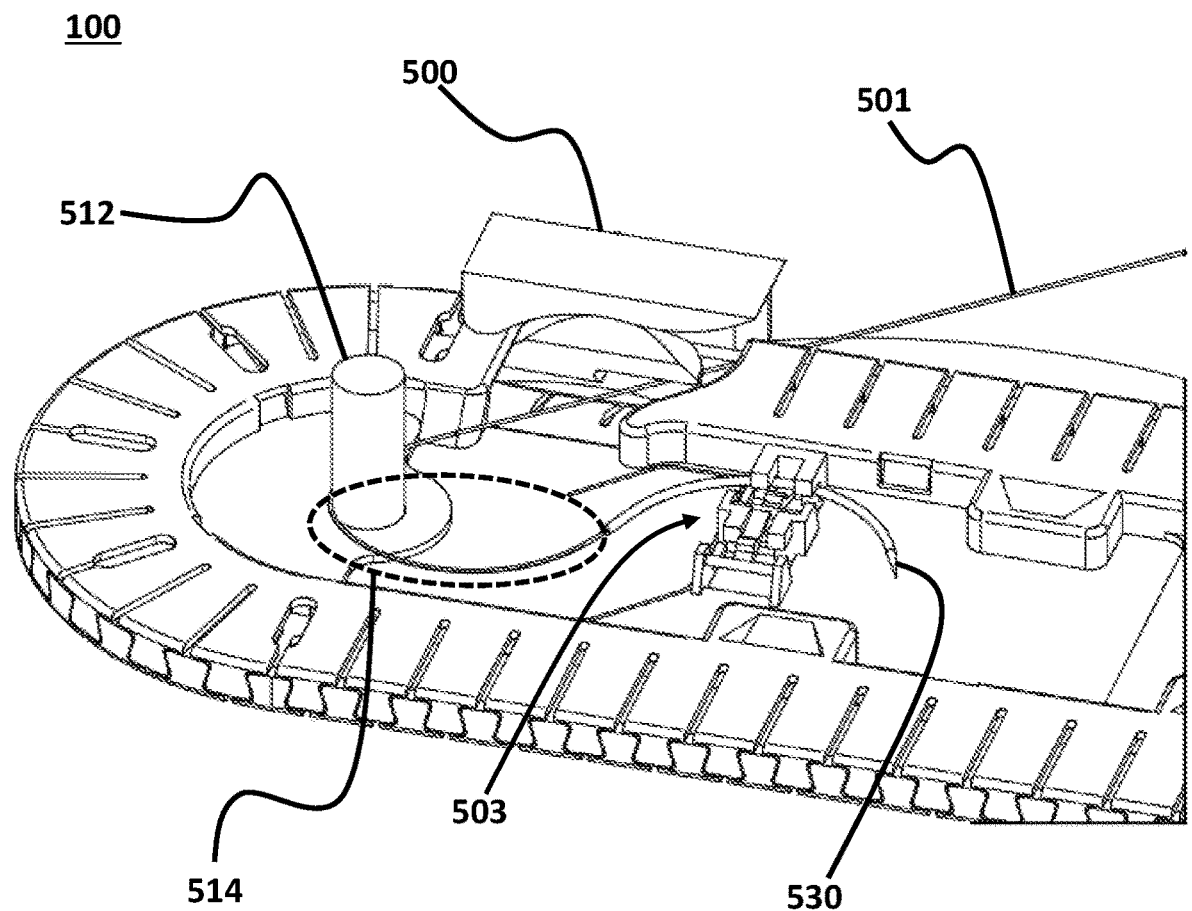
FIG. 5F illustrates a suture package in a scenario in which a zipper device is inserted into an entrance portion and, consequently, the zipper device is placed in a first closed path, consistent with one or more exemplary embodiments of the present disclosure.

In an exemplary embodiment, zipper device 500 may further include a suture guide channel 505. In an exemplary embodiment, suture guide channel 505 may receive suture 101 and keep suture 101 in touch with a distal end 552 of suture guide channel 505 during movement of zipper device 500 along first closed path 507. In an exemplary embodiment, suture guide channel 505 may further guide suture 101 to be placed inside peripheral winding channel 404 when zipper device 500 moves along first closed path 507. FIG. 5F shows suture package 100 in a scenario in which zipper device 500 is inserted into entrance portion 509 and, consequently, zipper device 500 is placed in first closed path 507, consistent with one or more exemplary embodiments of the present disclosure.

In an exemplary embodiment, as shown in FIG. 5E, suture package 100 may further include a first guide rod receiving hole 510. In an exemplary embodiment, first guide rod receiving hole 510 may be configured to receive a guide rod, for example, a first guide rod 512 (shown in FIG. 5F). In an exemplary embodiment, first guide rod 512 may be configured to keep a section of suture 501 at a predetermined position during movement of zipper device 500 along first closed path 507. For example, first guide rod 512 may keep a section 514 of suture 501 at a predetermined position during movement of zipper device 500 along first closed path 507. In an exemplary embodiment, it may be understood that, keeping section 514 of suture 501 at a predetermined position during movement of zipper device 500 along first closed path 507 may facilitate suture 501 placement within peripheral winding channel 404 and also suture removal from peripheral winding channel 404 without an incidence of a suture lock-up.

Figure 5G:
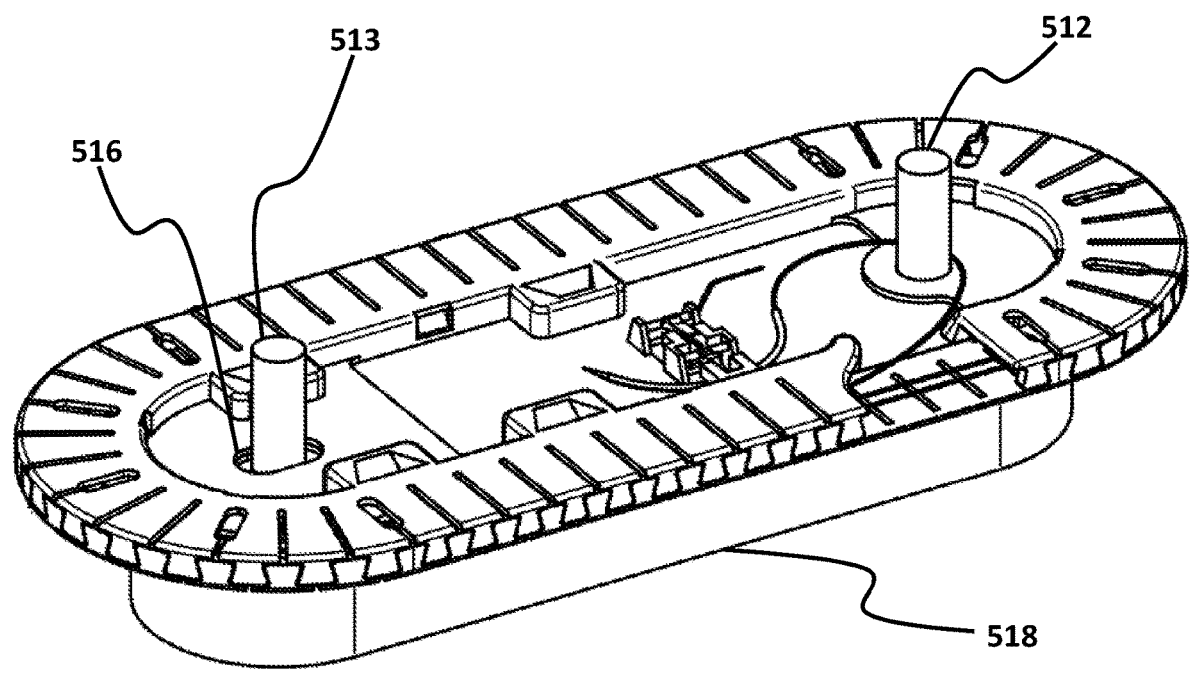
FIG. 5G illustrates a suture package fixed onto a base, consistent with one or more exemplary embodiments of the present disclosure.

FIG. 5G illustrates a suture package fixed onto a base, consistent with one or more exemplary embodiments of the present disclosure. In an exemplary embodiment, suture package 100 may further include a second guide rod receiving hole 516. In an exemplary embodiment, second guide rod receiving hole 516 may be configured to receive a guide rod, for example, a second guide rod 513 (shown in FIG. 5G). In an exemplary embodiment, second guide rod receiving hole 516 may have an elongated circle shape. In an exemplary embodiment, first guide rod 512 and second guide rod 513 may be attached to a base 518. In an exemplary embodiment, before inserting zipper device 500 into entrance portion 509, suture package 100 may be positioned and fixed onto base 518 through inserting first guide rod 512 into first guide receiving hole 510 and inserting second guide rod 513 into second guide rod receiving hole 516. In an exemplary embodiment, elongated circle shape of second guide receiving hole 516 may facilitate positioning and fixing of suture package 100 onto base 518.

Figure 6A:
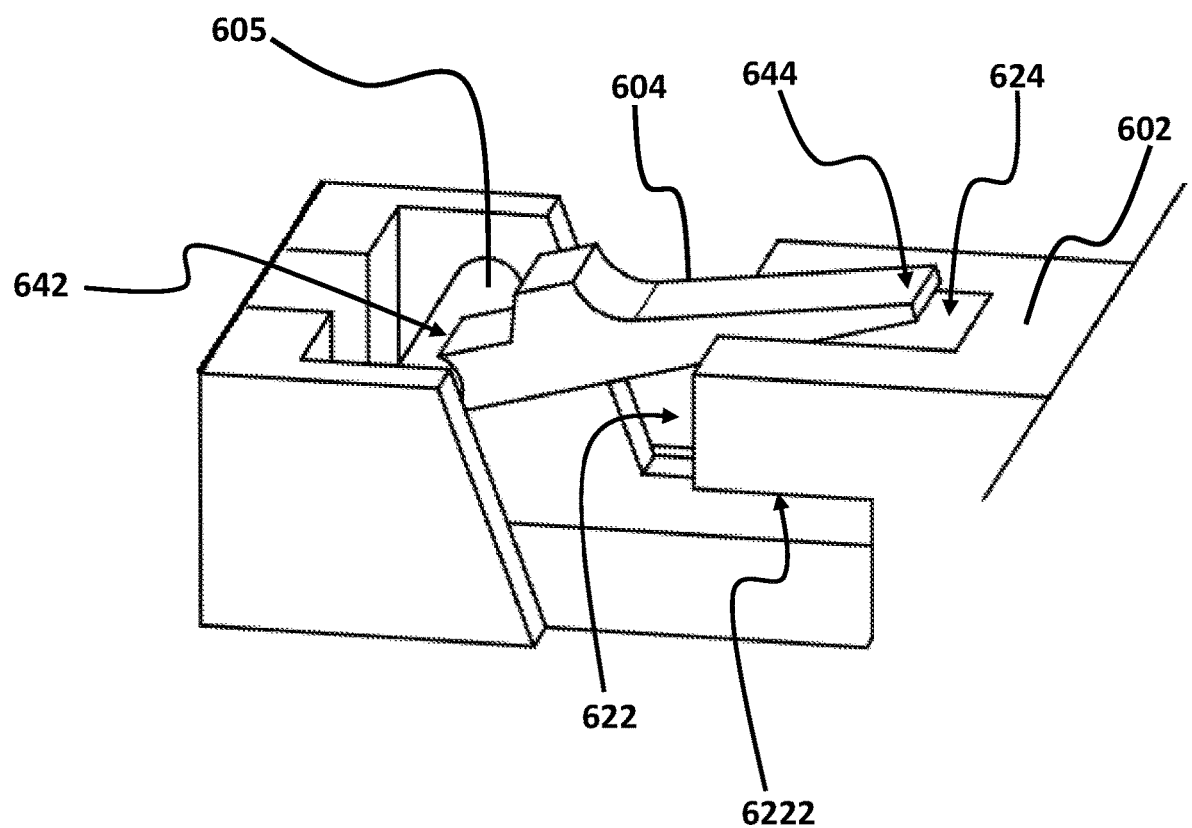
FIG. 6A illustrates a perspective view of a needle park, consistent with one or more exemplary embodiments of the present disclosure.

As further shown in FIG. 5F, in an exemplary embodiment, suture package 100 may further include a needle park 503. In an exemplary embodiment, needle park 503 may be configured to receive and hold a needle 530. In an exemplary embodiment, needle 530 may be attached to a head of suture 101. FIG. 6A shows a perspective view of needle park 503, consistent with one or more exemplary embodiments of the present disclosure. As shown in FIG. 6A, in an exemplary embodiment, needle park 503 may include a base element 602 and a flexible arm 604. In an exemplary embodiment, base element 602 may include a protruded edge 622 and a slot 624 beside protruded edge 622. In an exemplary embodiment, a proximal end 642 of flexible arm 604 may be attached to a torsional spring 605. In an exemplary embodiment, a distal end 644 of flexible arm 604 may be disposed inside slot 624. In an exemplary embodiment, flexible arm 604 may be configured to deflect inside slot 624 downwardly responsive to flexible arm 604 being pushed downward by a needle for example needle 530. In an exemplary embodiment, flexible arm 604 may further be configured to guide a needle, for example, needle 530 to be placed at a bottom side of protruded edge 622. In an exemplary embodiment, flexible arm 604 may secure a needle, for example, needle 530, between distal end 644 (of flexible arm 604) and a bottom surface 6222 (of protruded edge 622) through applying an upward force to needle 530 by torsional spring 605 and spring back force of flexible arm 604. In an exemplary embodiment, spring back force of flexible arm 604 may refer to a force that a deformed flexible arm 604 applies to needle 530 as flexible arm 604 may tend to retain its initial position.

Figure 6B:
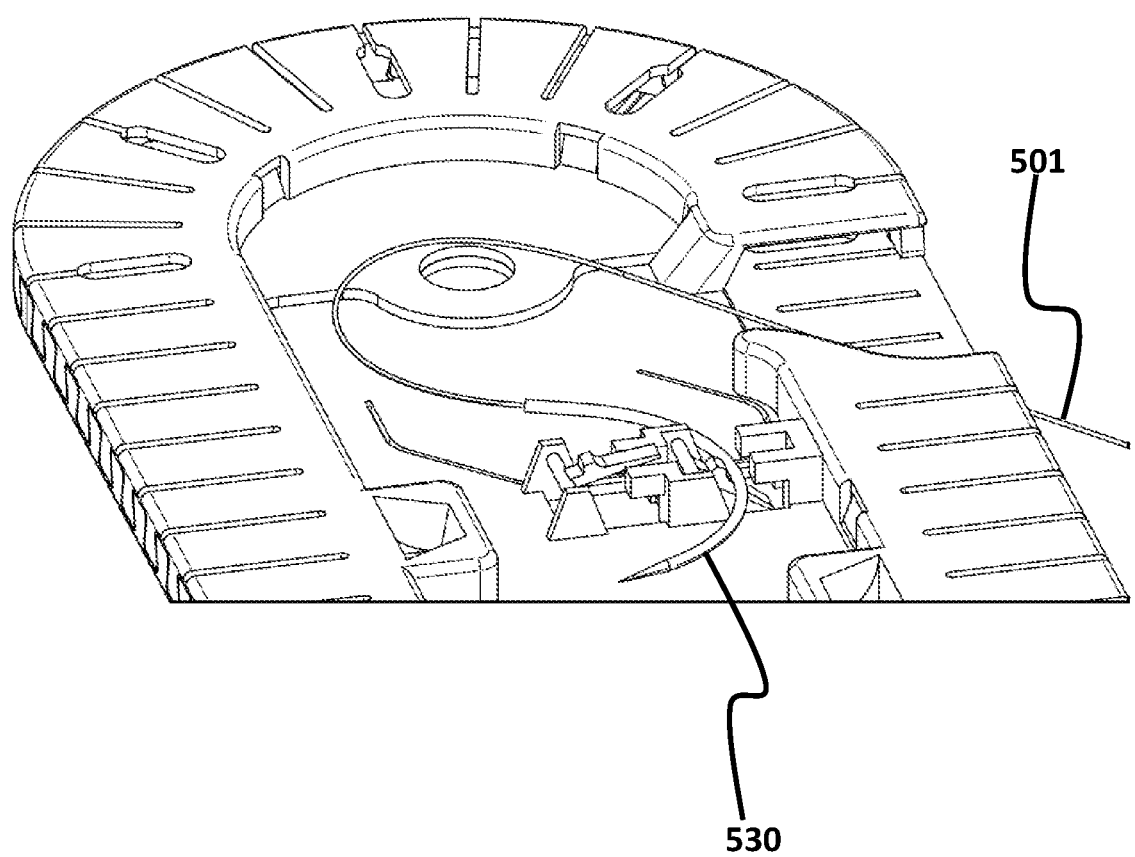
FIG. 6B illustrates a needle park in a scenario in which a flexible arm is pushed downward by a needle, consistent with one or more exemplary embodiments of the present disclosure.
Figure 6C:
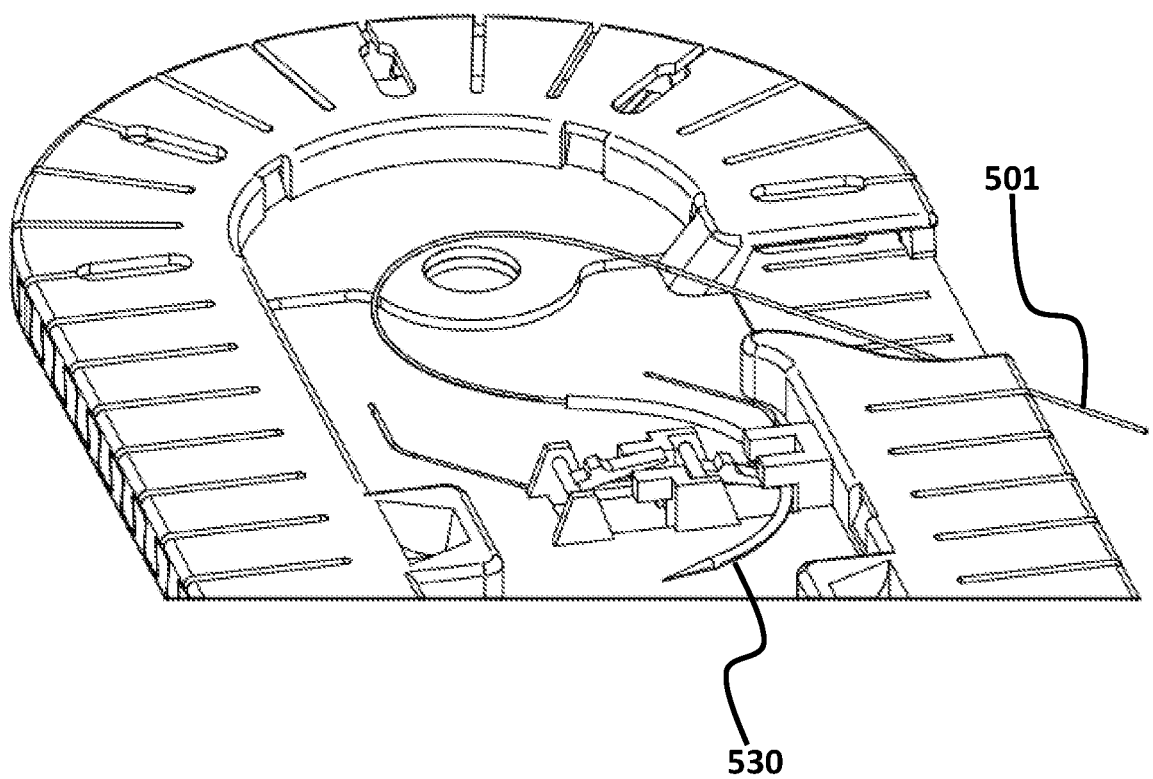
FIG. 6C illustrates a needle park in a scenario in which a needle is secured between a distal end of a flexible arm and a bottom surface of a protruded edge, consistent with one or more exemplary embodiments of the present disclosure.

FIG. 6B shows needle park 503 in a scenario in which flexible arm 604 is pushed downward by needle 530, consistent with one or more exemplary embodiments of the present disclosure. FIG. 6C shows needle park 503 in a scenario in which needle 530 is secured between distal end 644 (of flexible arm 604) and a bottom surface 6222 (of protruded edge 622), consistent with one or more exemplary embodiments of the present disclosure. In an exemplary embodiment, it may be understood that needle park 503 may provide a facility for a surgeon to easily remove needle 530 from suture package 100 when needle 530 is to be used.

Figure 7A:
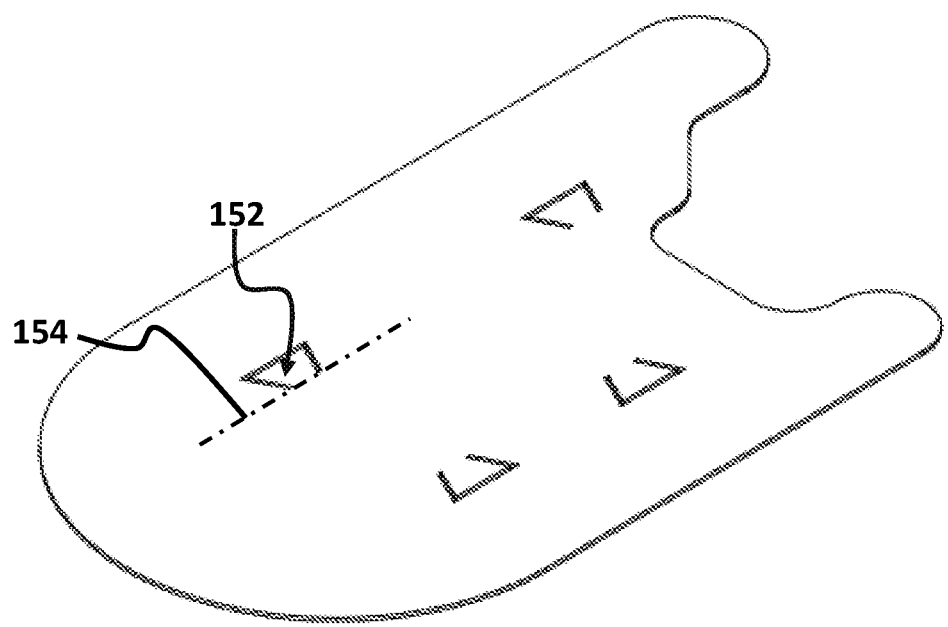
FIG. 7A illustrates a label used in a suture package, consistent with one or more exemplary embodiments of the present disclosure.
Figure 7B:
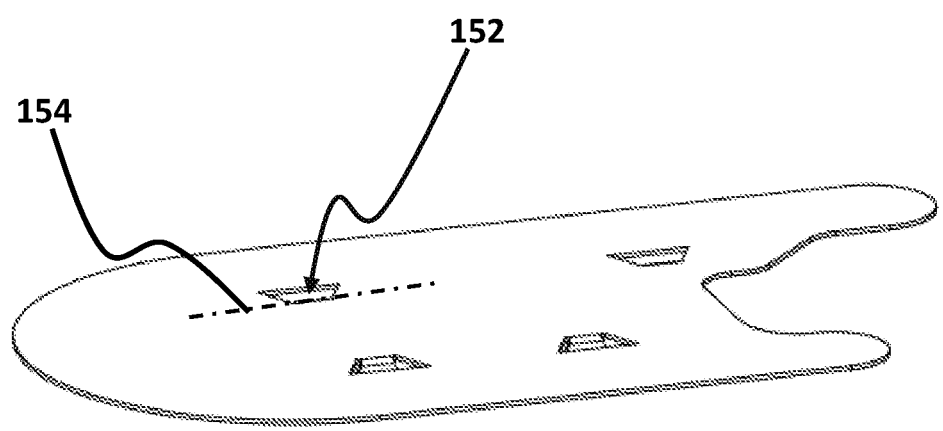
FIG. 7B illustrates a label in a scenario in which a label locker is in open position, consistent with one or more exemplary embodiments of the present disclosure.

Referring back to FIG. 1A, in an exemplary embodiment, suture package 100 may further include a label 105 configured to be attached to a top surface 141 of top member 104. FIG. 7A shows label 105, consistent with one or more exemplary embodiments of the present disclosure. As shown in FIG. 7A, in an exemplary embodiment, label 105 may include a label locker 152 having a trapezoidal shape. In an exemplary embodiment, label locker 152 may have any other shapes such as triangular shape, circular shape, and rectangular shape. In an exemplary embodiment, label locker 152 may be configured to rotate around a first axis 154. In an exemplary embodiment, first axis 154 may be an axis passing through an edge of label locker 152 which connects label locker 152 to label 105. In an exemplary embodiment, label locker 152 may be in an open position or a closed position. In an exemplary embodiment, label locker 152 may convert from the open position to the closed position or from the closed position to the open position by rotating around first axis 154. FIG. 7B shows label 105 in a scenario in which label locker 152 is in the open position, consistent with one or more exemplary embodiments of the present disclosure. In an exemplary embodiment, when label locker 152 is in the closed position, label 105 may be not engaged with top member 104. In an exemplary embodiment, when label 105 is not engaged with top member 104, a person may be able to separate label 105 from top member 104. In an exemplary embodiment, when label locker 152 is in the open position, label 105 may be engaged with top member 104. In an exemplary embodiment, when label 105 is engaged with top member 104, a person may not be able to separate label 105 from top member 104.

Figure 8A:
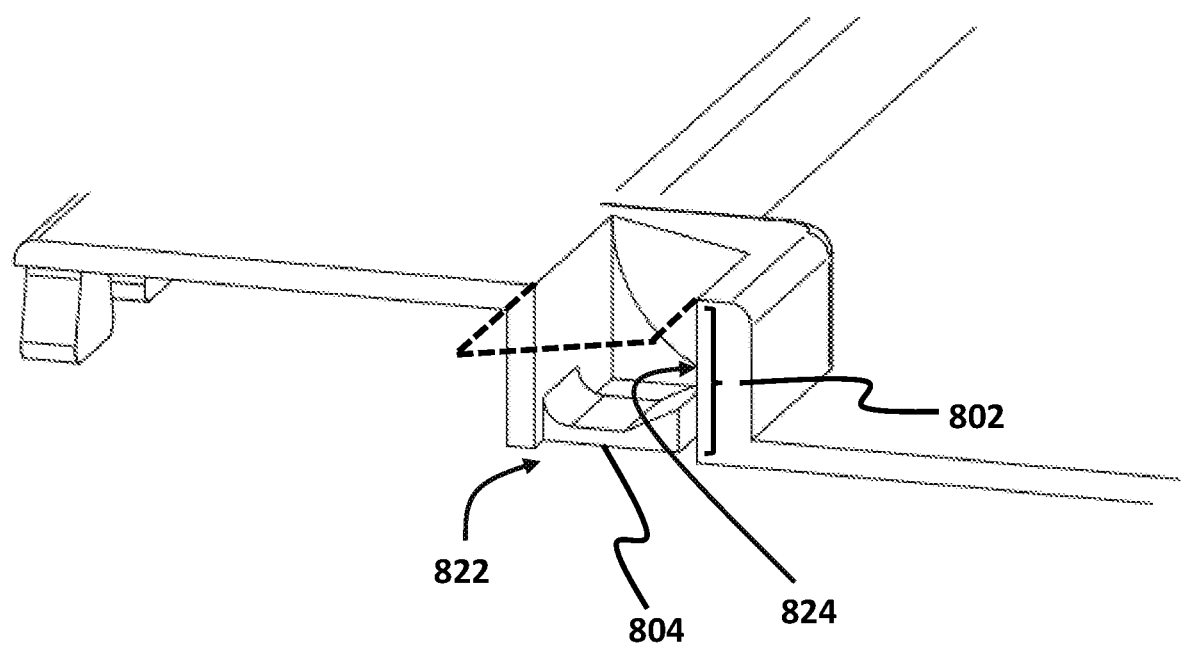
FIG. 8A illustrates a sectional view of a trapping mechanism, consistent with one or more exemplary embodiments of the present disclosure.

Referring back to FIG. 3, in an exemplary embodiment, top member 104 may include a trapping mechanism 143. FIG. 8A shows a sectional view of trapping mechanism 143, consistent with one or more exemplary embodiments of the present disclosure. As shown in FIG. 8A, in an exemplary embodiment, trapping mechanism 143 may include a trapezoidal hole 802 associated with label locker 152. In an exemplary embodiment, label locker 152 may be configured to rotate inside trapezoidal hole 802. In an exemplary embodiment, trapping mechanism 143 may further include a label gripper 804 disposed at a bottom section 822 of trapezoidal hole 802. In an exemplary embodiment, label gripper 804 may be configured to bend downwardly responsive to label locker 152 pushing down label gripper 804 during rotation of label gripper 804 inside trapezoidal hole 802. Furthermore, label gripper 804 may further be configured to trap label locker 152 between label gripper 804 and an inner surface 824 of trapezoidal hole 802. In an exemplary embodiment, trapping label locker 152 between label gripper 804 and inner surface 824 of trapezoidal hole 802 may refer to putting label locker 152 between label gripper 804 and an inner surface 824 of trapezoidal hole 802 in such a way that label gripper 804 is prevented from being released.

Figure 8B:
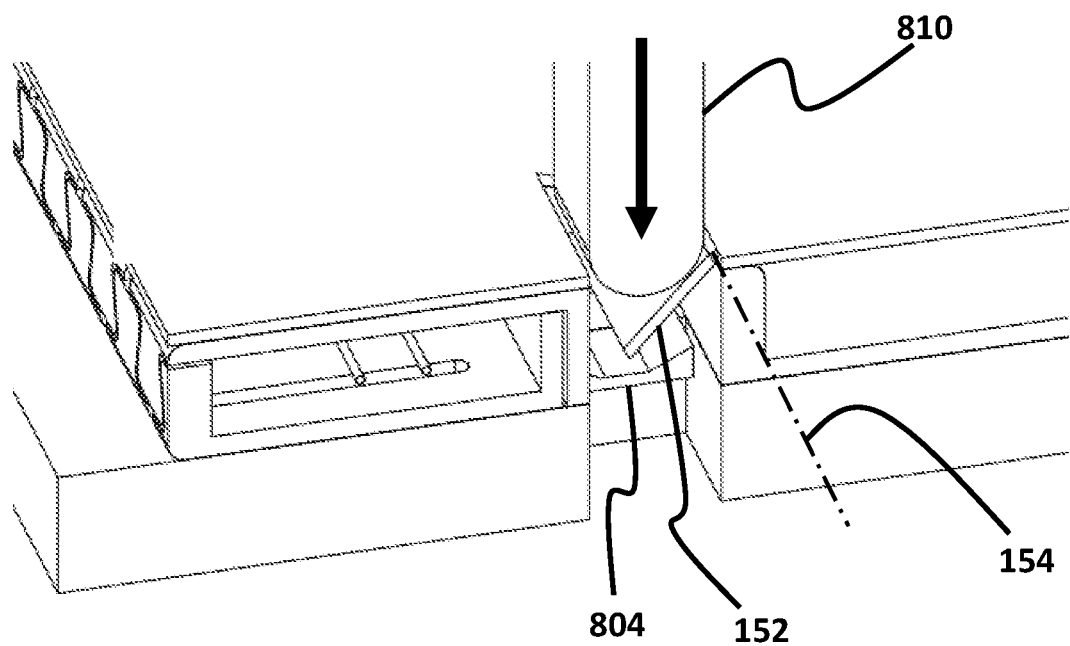
FIG. 8B illustrates a trapping mechanism in a scenario in which a label locker is rotated around a first axis, consistent with one or more exemplary embodiments of the present disclosure.
Figure 8C:
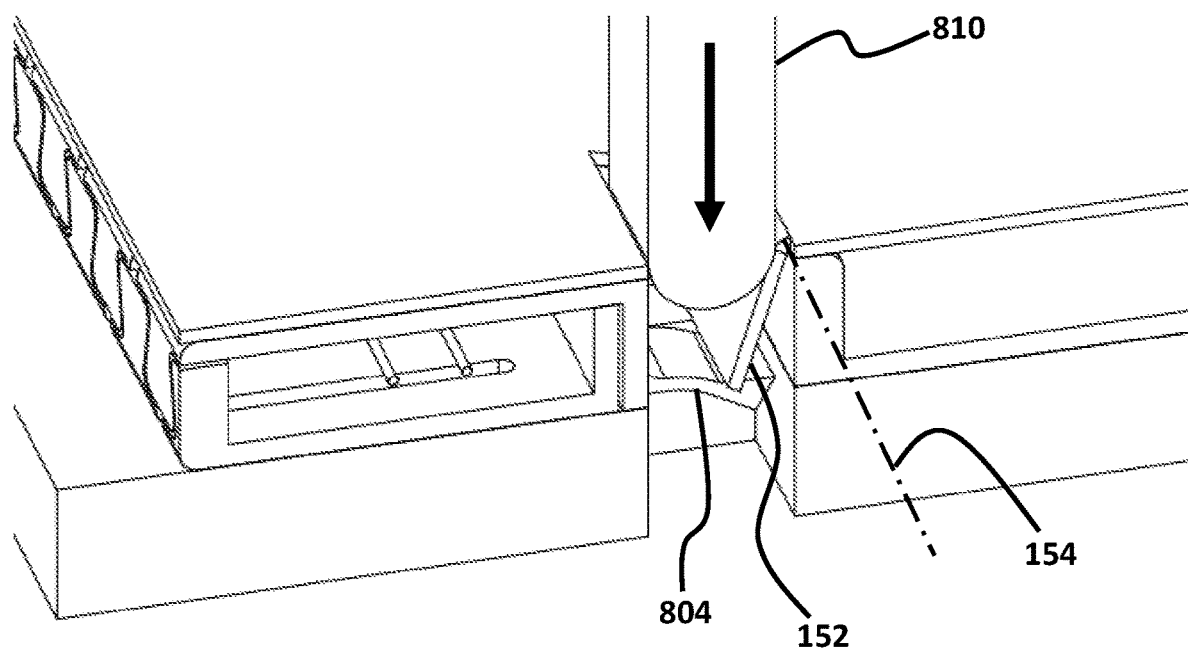
FIG. 8C illustrates a trapping mechanism in a scenario in which a label gripper is bent downwardly due to ration of a label locker around a first axis, consistent with one or more exemplary embodiments of the present disclosure.
Figure 8D:
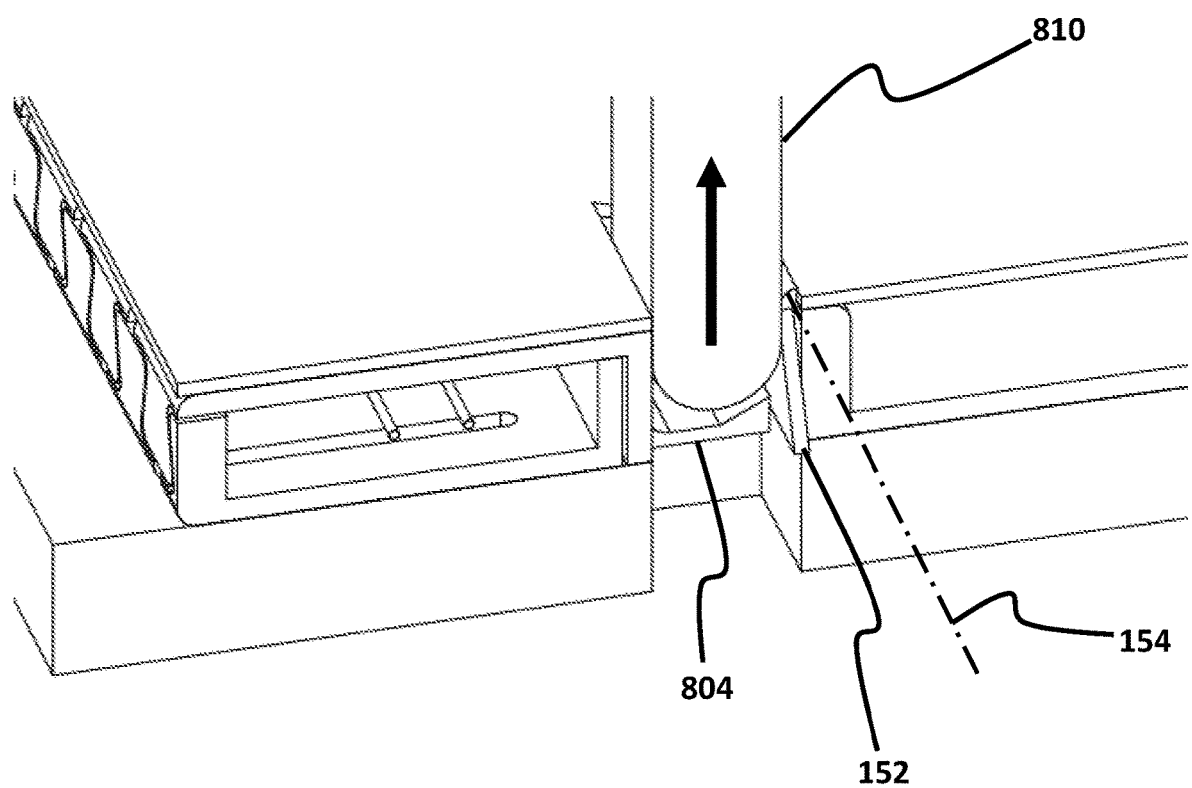
FIG. 8D illustrates a trapping mechanism in a scenario in which a label locker is trapped between a label gripper and an inner surface of a trapezoidal hole, consistent with one or more exemplary embodiments of the present disclosure.

FIG. 8B shows trapping mechanism 143 in a scenario in which label locker 152 is rotated around first axis 154, consistent with one or more exemplary embodiments of the present disclosure. As shown in FIG. 8B, in an exemplary embodiment, label locker 152 may be pushed down and, thereby, rotated around first axis 154 by utilizing an external rod 810. FIG. 8C shows trapping mechanism 143 in a scenario in which label gripper 804 is bent downwardly due to ration of label locker 152 around first axis 154, consistent with one or more exemplary embodiments of the present disclosure. FIG. 8D shows trapping mechanism 143 in a scenario in which label locker 152 is trapped between label gripper 804 and an inner surface 824 of trapezoidal hole 802, consistent with one or more exemplary embodiments of the present disclosure. As shown in FIG. 8D, in an exemplary embodiment, when label locker 152 is rotated by an amount of about 90 degrees, label gripper 804 may return to its initial position and label locker 152 may be trapped between label gripper 804 and an inner surface 824 of trapezoidal hole 802. In an exemplary embodiment, trapping label locker 152 between label gripper 804 and inner surface 824 of trapezoidal hole 802 may refer to putting label locker 152 between label gripper 804 and an inner surface 824 of trapezoidal hole 802 in such a way that label gripper 804 is prevented from being released.

Figure 9A:
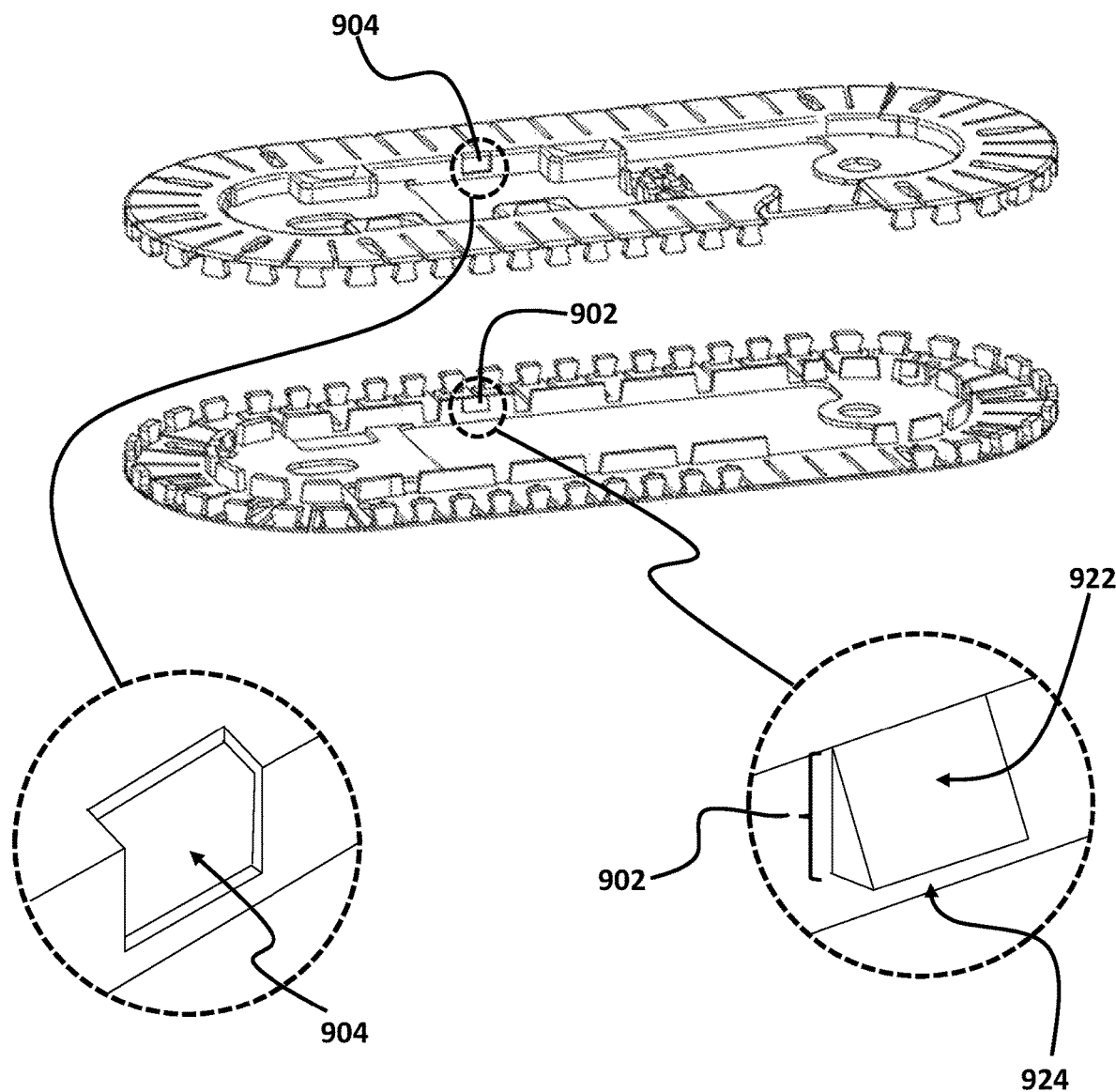
FIG. 9A illustrates a base member and a top member, consistent with one or more exemplary embodiments of the present disclosure.
Figure 9B:
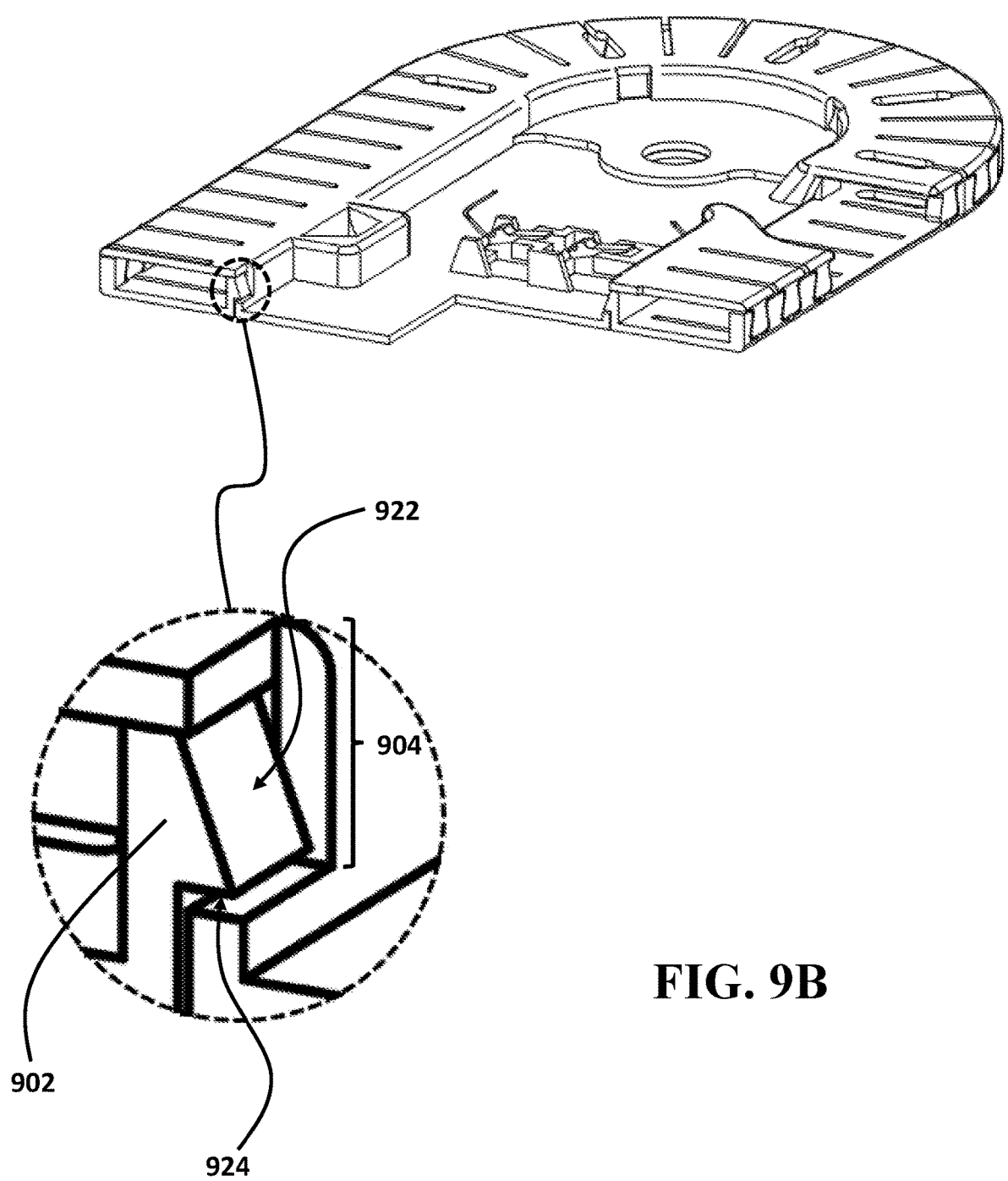
FIG. 9B illustrates a lock mechanism in a scenario in which a wedge-shaped member is inserted into a lock hole, consistent with one or more exemplary embodiments of the present disclosure.

FIG. 9A shows base member 102 and top member 104, consistent with one or more exemplary embodiments of the present disclosure. In an exemplary embodiment, suture package 100 may further include a lock mechanism. As shown in FIG. 9A, in an exemplary embodiment, the lock mechanism may include a wedge-shaped member 902 attached to an inner surface 228 of base member 102. In an exemplary embodiment, wedge-shaped member 902 may include an inclined surface 922 and a bottom surface 924. In an exemplary embodiment, the lock mechanism may further include a lock hole 904 provided at an inner surface 328 of top member 104. In an exemplary embodiment, lock hole 904 may be associated with wedge-shaped member 902. In an exemplary embodiment, lock hole 904 may be configured to receive wedge-shaped member 902. In an exemplary embodiment, inclined surface 922 of wedge-shaped member 902 may be configured to allow wedge-shaped member 902 to be inserted into lock hole 904. In an exemplary embodiment, bottom surface 924 of wedge-shaped member 902 may be configured to prevent wedge-shaped member 902 to exit from lock hole 904. In an exemplary embodiment, it may be understood that by pushing down top member 104 to base member 102, wedge-shaped member 902 may be inserted into lock hole 904 and, consequently, top member 104 and base member 102 may be coupled to each other. FIG. 9B shows the lock mechanism in a scenario in which wedge-shaped member 902 is inserted into lock hole 904, consistent with one or more exemplary embodiments of the present disclosure. In an exemplary embodiment, the lock mechanism may be replaced by any other mechanism that is able to attach top member 104 to base member 102. For example, top member 104 may be attached to base member 102 by ultrasonic welding.

While the foregoing has described what may be considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective spaces of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A suture package for storing sutures armed with needles, the suture package comprising:
   a base member with a base outer periphery, the base member comprising a base outer wall extending upwardly from a top side of the base member and along the base outer periphery, the base outer wall comprising a plurality of base teeth and a plurality of base intercostal spaces, the plurality of base teeth and the plurality of base intercostal spaces arranged alternatively around the base outer periphery;
   a top member with a top outer periphery, the top member comprising a top outer wall extending downwardly from a bottom side of the top member and along the top outer periphery, the top outer wall comprising a plurality of top teeth and a plurality of top intercostal spaces, the plurality of top teeth and the plurality of top intercostal spaces arranged alternatively around the top outer periphery, each respective top tooth from the plurality of top teeth associated with a respective base intercostal space from the plurality of base intercostal spaces, each respective top tooth from the plurality of top teeth configured to fill the respective base intercostal space from the plurality of base intercostal spaces, each respective top intercostal space from the plurality of top intercostal spaces associated with a respective base tooth from the plurality of base teeth, each respective base tooth from the plurality of base teeth configured to fill the respective top intercostal space from the plurality of top intercostal spaces, the base outer wall and the top outer wall configured to form an engaged outer wall responsive to:
      one or more base teeth from the plurality of base teeth filling respective top intercostal spaces from the plurality of top intercostal spaces;
      one or more top teeth from the plurality of top teeth filling respective base intercostal spaces from the plurality of base intercostal spaces;
   a peripheral winding channel formed between the top side of the base member, the bottom side of the top member, and an inner side of the engaged outer wall; and
   a zipper device, comprising:
      a top edge comprising a bottom curved surface;
      a bottom edge comprising a top curved surface; and
      an oval-shaped opener disposed between the top curved surface and the bottom curved surface, the oval-shaped opener comprising:
         a top oval surface, the top oval surface and the bottom curved surface defining a top curved path between the oval-shaped opener and the top edge, the top curved path associated with the top outer wall, the top oval surface and the bottom curved surface configured to guide a section of the top outer wall to move along the top curved path;
         a bottom oval surface, the bottom oval surface and the top curved surface defining a bottom curved path between the oval-shaped opener and the bottom edge, the bottom curved path associated with the base outer wall, the bottom oval surface and the top curved surface configured to guide a section of the base outer wall to move along the bottom curved path;
      wherein the zipper device is configured to disengage and then reengage a section of the engaged outer wall responsive to the zipper device passing through a first closed path at the section of the engaged outer wall, the first closed path associated with the engaged outer wall.

2. The suture package of claim 1, wherein the zipper device comprises an opener head, the opener head configured to:
  disengage the section of the engaged outer wall through splitting the engaged outer wall responsive to the zipper device moving along the first closed path;
  guide a first top tooth from the plurality of top teeth to enter the top curved path after splitting the engaged outer wall, the first top tooth associated with the section of the engaged outer wall; and
  guide a first base tooth from the plurality of base teeth to enter the bottom curved path after splitting the engaged outer wall, the first base tooth associated with the section of the engaged outer wall.

3. The suture package of claim 2, wherein a distal end of the top edge and a distal end of the bottom edge are configured to reengage a section of the base outer wall exiting the bottom curved path with an associated section of the top outer wall exiting the top curved path through:
  urging a second top tooth from the plurality of top teeth to fill a respective base intercostal space from the plurality of base intercostal spaces; and
  urging a second base tooth from the plurality of base teeth to fill a respective top intercostal space from the plurality of top intercostal spaces.

4. The suture package of claim 3, wherein the engaged outer wall comprises an entrance portion, the zipper device configured to be placed in the first closed path responsive to the zipper device being inserted into the entrance portion.

5. The suture package of claim 4, wherein the zipper device further comprises a suture guide channel, the suture guide channel configured to:
  receive the suture;
  keep the suture in touch with an end of the suture guide channel during movement of the zipper device along the first closed path; and
  guide the suture to be placed inside the peripheral winding channel responsive to movement of the zipper device along the first closed path.

6. The suture package of claim 5, further comprising a needle park configured to receive and hold a needle, the needle park comprising:
  a base element, comprising:
    a protruded edge; and
    a slot, the slot present immediately next to the protruded edge; and
  a flexible arm, a proximal end of the flexible arm attached to a torsional spring, a distal end of the flexible arm disposed inside the slot, the flexible arm configured to:
    deflect downwardly inside the slot responsive to the distal end of the flexible arm being pushed downward;
    guide the needle to be placed at a bottom side of the protruded edge; and
    secure the needle between the distal end of the flexible arm and a bottom surface of the protruded edge through applying an upward force to the needle, the upward force associated with the torsional spring.

7. The suture package of claim 6, further comprising a first guide rod receiving hole, the first guide rod receiving hole configured to receive a first guide rod, the first guide rod configured to keep a section of the suture at a predetermined position during movement of the zipper device along the first closed path.

8. The suture package of claim 7, wherein:
  the base member further comprises a plurality of base flexible blades arranged around a base inner periphery of the base member, each respective base flexible blade from the plurality of base flexible blades associated with a respective base tooth from the plurality of base teeth, each respective base tooth attached to a distal end of the respective base flexible blade, each respective base flexible blade configured to facilitate movement of the respective base tooth along the bottom curved path; and
  the top member further comprises a plurality of top flexible blades arranged around a top inner periphery of the top member, each respective top flexible blade from the plurality of top flexible blades associated with a respective top tooth from the plurality of top teeth, the respective top tooth attached to a distal end of the respective top flexible blade, the respective top flexible blade configured to facilitate movement of the respective top tooth along the top curved surface.

9. The suture package of claim 8, further comprising a label attached to a top surface of the top member, the label comprising a label locker having a trapezoidal shape, the label locker configured to rotate around a first axis, the first axis passing through a common edge of the label locker and the label.

10. The suture package of claim 9, wherein the top member further comprises a trapping mechanism, the trapping mechanism comprising:
  a trapezoidal hole associated with the label locker; the label locker configured to rotate inside the trapezoidal hole; and
  a label gripper disposed at a bottom section of the trapezoidal hole, the label gripper configured to:
    bend downwardly responsive to the label locker pushing down the label gripper during rotation of the label gripper inside the trapezoidal hole; and
    trap the label locker between the label gripper and an inner surface of the trapezoidal hole.

11. The suture package of claim 10, further comprising a lock mechanism, the lock mechanism comprising:
  a wedge-shaped member attached to an inner surface of the base member, the wedge-shaped member comprising an inclined surface and a bottom surface; and
  a lock hole provided at an inner surface of the top member, the lock hole associated with the wedge-shaped member, the lock hole configured to receive the wedge-shaped member, the inclined surface configured to allow the wedge-shaped member to be inserted into the lock hole, the bottom surface configured to prevent the wedge-shaped member to exit from the lock hole.

12. The suture package of claim 11, further comprising a second guide rod receiving hole, the second guide rod receiving hole configured to receive a second guide rod, the suture package configured to be positioned and fixed onto a base attached to the first guide rod and the second guide rod through inserting the first guide rod into the first guide rod receiving hole and inserting the second guide rod into the second guide rod receiving hole.

13. The suture package of claim 12, wherein:
  the first guide rod receiving hole comprises a circular shape, and
  the second guide rod receiving hole comprises an elongated circular shape.

* * * * *